US009234893B2

(12) United States Patent
Cho et al.

(10) Patent No.: US 9,234,893 B2
(45) Date of Patent: Jan. 12, 2016

(54) MARKER COMPRISING ANTI-CK8/18 COMPLEX AUTOANTIBODY AND ITS USE FOR DIAGNOSING CANCER

(75) Inventors: Eun Wie Cho, Daejeon (KR); Chang Gyu Heo, Daejeon (KR); Jeong Heon Ko, Daejeon (KR); Mi Kyung Woo, Daejeon (KR); Hyang Sook Yoo, Daejeon (KR); Hai Min Hwang, Daejeon (KR)

(73) Assignees: Korea Research Institute of Bioscience and Biotechnology; Daejeon, Republic of Korea ( * ) Notice: Subject to any disclaimer, the term of this patent is extended or adjusted under 35 U.S.C. 154(b) by 19 days.

(21) Appl. No.: 14/000,221

(22) PCT Filed: Feb. 20, 2012

(86) PCT No.: PCT/KR2012/001264
§ 371 (c)(1),
(2), (4) Date: Oct. 22, 2013

(87) PCT Pub. No.: WO2012/112013
PCT Pub. Date: Aug. 23, 2012

(65) Prior Publication Data
US 2014/0093892 A1    Apr. 3, 2014

(30) Foreign Application Priority Data

Feb. 18, 2011 (KR) .................... 10-2011-0014809
Feb. 3, 2012  (KR) .................... 10-2012-0011503

(51) Int. Cl.
*C07K 16/18*   (2006.01)
*G01N 33/574*  (2006.01)
*C07K 7/06*    (2006.01)
*C07K 16/30*   (2006.01)

(52) U.S. Cl.
CPC .............. *G01N 33/574* (2013.01); *C07K 7/06* (2013.01); *C07K 16/18* (2013.01); *C07K 16/30* (2013.01); *G01N 33/57415* (2013.01); *C07K 2317/32* (2013.01); *C07K 2317/34* (2013.01); *G01N 2333/4742* (2013.01)

(58) Field of Classification Search
None
See application file for complete search history.

(56) References Cited

U.S. PATENT DOCUMENTS

2003/0119079 A1*  6/2003  Hanash et al. ............... 435/7.23
2004/0214272 A1* 10/2004  La Rosa et al. ............. 435/69.1
2009/0311193 A1* 12/2009  Mauro et al. ................ 424/9.6

FOREIGN PATENT DOCUMENTS

| EP | 1062515 | 12/2000 |
| KR | 10-2010-0118900 | 11/2010 |
| KR | 10-2011-0040624 | 4/2011 |
| WO | WO 2010/126279 | 11/2010 |
| WO | WO 2011/046309 | 4/2011 |
| WO | WO 2012/112013 | 8/2012 |

OTHER PUBLICATIONS

International Search Report and the Written Opinion Dated Sep. 24, 2012 From the International Searching Authority Re. Application No. PCT/KR2012/001264.

Bluemke et al. "Detection of Circulating Tumor Cells in Peripheral Blood of Patients With Renal Cell Carcinoma Correlates With Prognosis", Cancer Epidemiology, Biomarkers & Prevention, 18(8): 2190-2194, Aug. 5, 2009. Abstract, Fig.2, Discussion.

Cimpean et al. "Relevance of the Immunohistochemical Expression of Cytokeratin 8/18 for the Diagnosis and Classification of Breast Cancer", Romanian Journal of Morphology and Embryology, 49(4): 479-483, 2008. Abstract, Figs.1-3, Conclusions.

Mulligan et al. "CK8/18 Expression, the Basal Phenotype, and Family History in Identifying BRCA1-Associated Breast Cancer in the Ontario Site of the Breast Cancer Family Registry", Cancer, 117: 1350-1359, Apr. 1, 2011.

Translation of Notice of Preliminary Rejection Dated Aug. 19, 2013 From the Korean Intellectual Property Office Re. Application No. 10-2012-0011503.

Martinez-Iglesias et al. "Hypothyroidism Enhances Tumor Invasiveness and Metastasis Development", PLoS One, 4(7): e6428-1-e6428-11, Jul. 29, 2009.

* cited by examiner

*Primary Examiner* — Brad Duffy
*Assistant Examiner* — Nelson B Moseley, II

(57) ABSTRACT

The present invention relates to a cytokeratin 8/18 complex-specific autoantibody or a fragment comprising an antigen-binding site (paratope) thereof, the use thereof in the diagnosis of breast cancer, a polypeptide having an amino acid sequence of an epitope specifically binding to the autoantibody, a composition for diagnosing breast cancer comprising an agent capable of measuring an expression level of the autoantibody or the fragment comprising an antigen-binding site thereof, a hybridoma cell line producing the autoantibody, and a kit for diagnosing breast cancer comprising the composition of the present invention. Further, the present invention relates to a method for diagnosing breast cancer, comprising the step of detecting the cytokeratin 8/18 complex-specific autoantibody or the fragment comprising the antigen-binding site thereof using the composition of the present invention, and a method for screening a therapeutic agent for breast cancer using the autoantibody.

9 Claims, 12 Drawing Sheets

Fig. 3
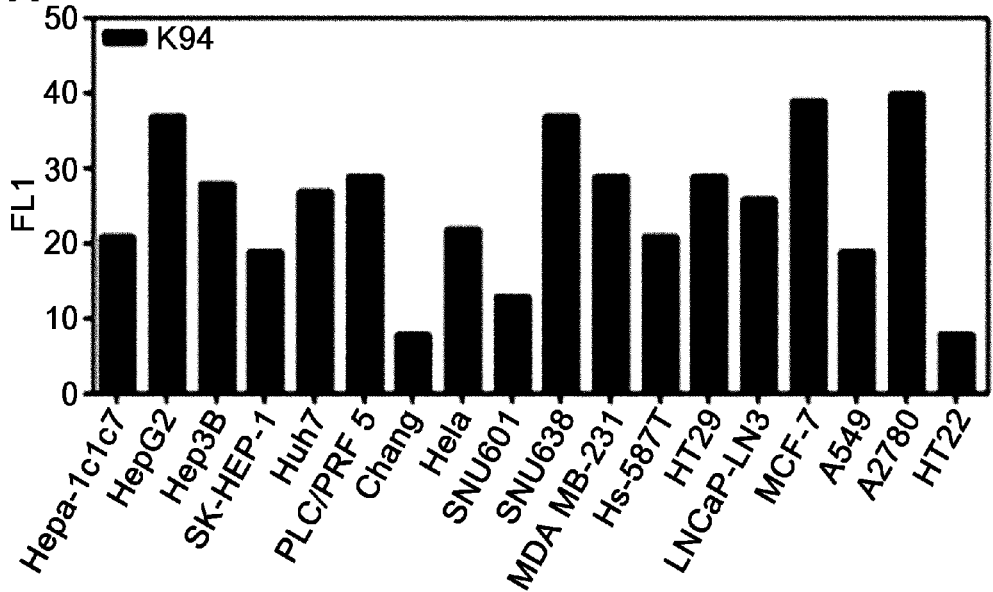
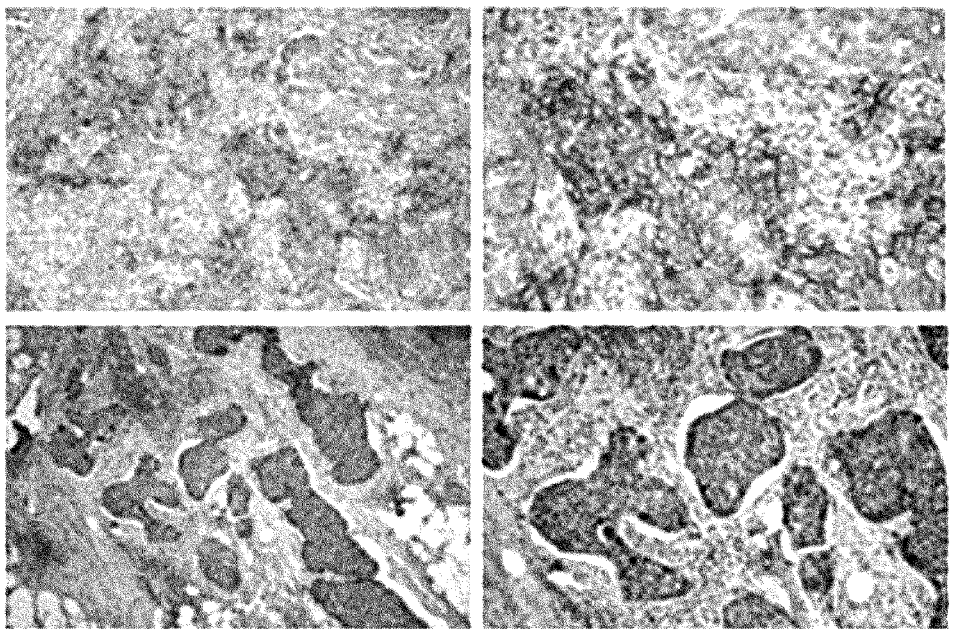

SAG GTT MAG CTG SAG CAG TCW GGC CCT GGG ATA TTG CAG CCC TCC CAG ACC CTC AGT CTG ACT TGT TCT TTC
 X   V   X   L   X   Q   S   G   P   G   I   L   Q   P   S   Q   T   L   S   L   T   C   S   F

TCT GGG TTT TCA CTG AGC ACT TTT GGT ATG GGT GTA GGC TGG ATT CGT CAG CCT TCA GGG AAG GGT CTG GAG
 S   G   F   S   L   S   T   F   G   M   G   V   G   W   I   R   Q   P   S   G   K   G   L   E

|CDR-H1:a.a.26-37|                    |CDR-H2:a.a.52-67|

TGG CTG GCA CAC ATT TGG GAT GAT GAT AAG TAC TAT AAC CAG GCC CTG AAG AGT CGG CTC ACA ATC TCC
 W   L   A   H   I   W   D   D   D   K   Y   Y   N   Q   A   L   K   S   R   L   T   I   S

AAG GAT ACC TCC AAA AAC CAG GTA TTC CTC AAG ATC GCC AAT GTG GAC ACT GCA GAT ACT GCC ACA TAC TAC
 K   D   T   S   K   N   Q   V   F   L   K   I   A   N   V   D   T   A   D   T   A   T   Y   Y

|CDR-H3:a.a.100-113|

TGT GCT CGA ATA GGA GGC TAC TAC GGT AGT AGC TCC TGG TAC TTC GAT GTC TGG GGC ACA GGG ACC ACG GTC
 C   A   R   I   G   G   Y   Y   G   S   S   S   W   Y   F   D   V   W   G   T   G   T   T   V

ACC GTC TCC TCA GAG AGT CAG TCC TTC CCA AAT GTC AGA TCT TCC
 T   V   S   S   E   S   Q   S   F   P   N   V   R   S   S

GAT ATT GTG ATC ACA CAA ACT CCA TCC TCA CTG TCT GCA TCT CTG GGA GGC AAA GTC ACC ATC ACT TGC AAG
 D   I   V   I   T   Q   T   P   S   S   S   L   S   A   S   L   G   G   K   V   T   I   T   C   R

GCA AGC CAA GAC ATT AAC AAG TAT ATA GCT TGG TAC CAA CAC AAG CCT GGA AAA GGT CCT AGG CTG CTC ATA
 A   S   Q   D   I   N   K   Y   I   A   W   Y   Q   H   K   P   G   K   G   P   R   L   L   I
     CDR-L1:a.a.24-34

CAT TAC ACA TCT ACA TTA CAG CCA GGC ATC CCA TCA AGG TTC AGT GGC AGT GGG TCT GGG AGA GAT TAT TCC
 H   Y   T   S   T   L   Q   P   G   I   P   S   R   F   S   G   S   G   S   G   R   D   Y   S
                                         CDR-L2:a.a.60-66

TTC AGC ATC AGC AAC CTG GAG CCT GAA GAT ATT GCA ACT TAT TAT TGT CTA CAG TAT GAT AAT CTT CTC ACG
 F   S   I   S   N   L   E   P   E   D   I   A   T   Y   Y   C   L   Q   Y   D   N   L   L   T
                                                             CDR-L3:a.a.89-96

TTC GGA GGG GGG ACC AAG CTG GAA ATA AAA CGG GCT GAT GCT GCA CCA ACT GTA TCC
 F   G   G   G   T   K   L   E   I   K   R   A   D   A   A   P   T   V   S

Fig. 5
A
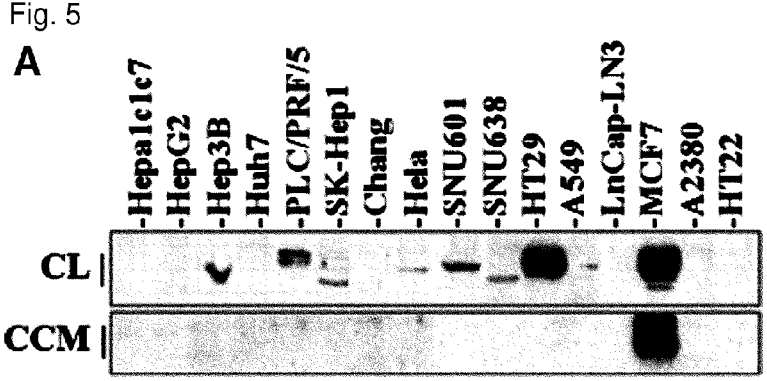
B
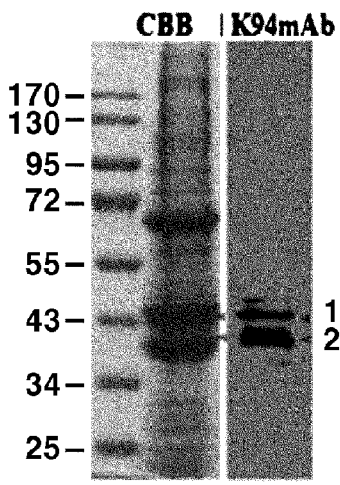
Fig. 6a
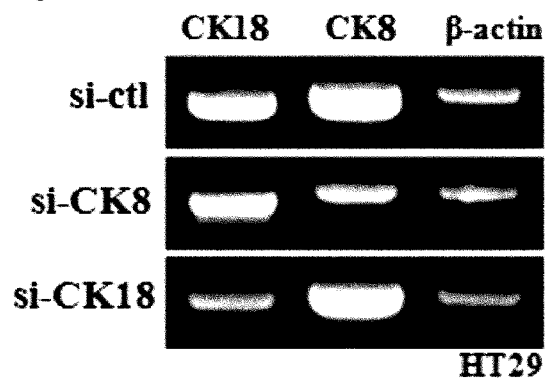
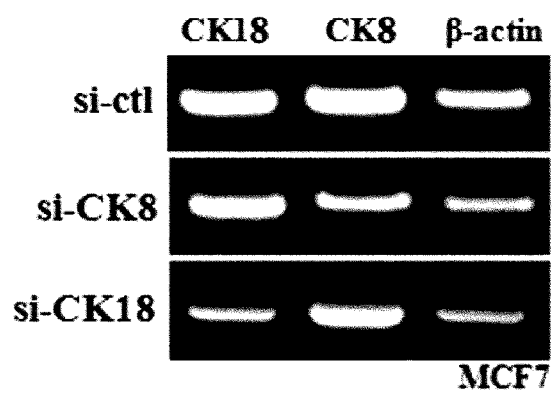

Fig. 6b
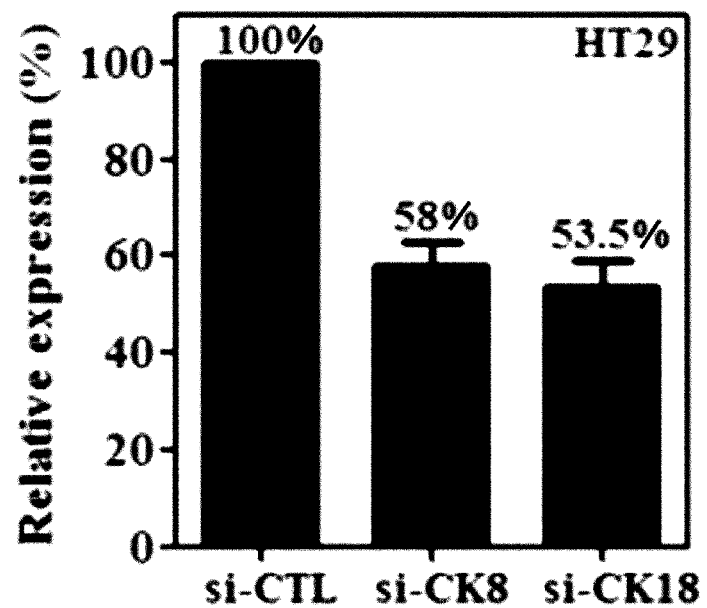
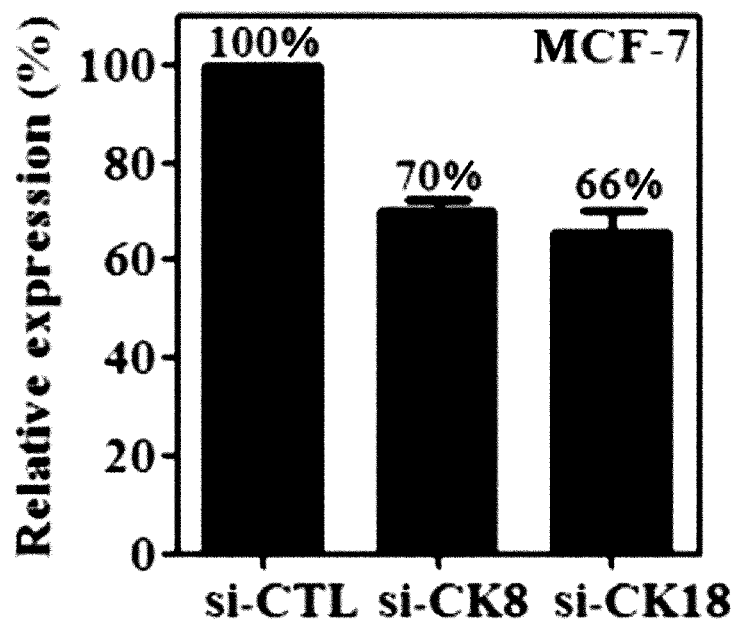

Fig. 7
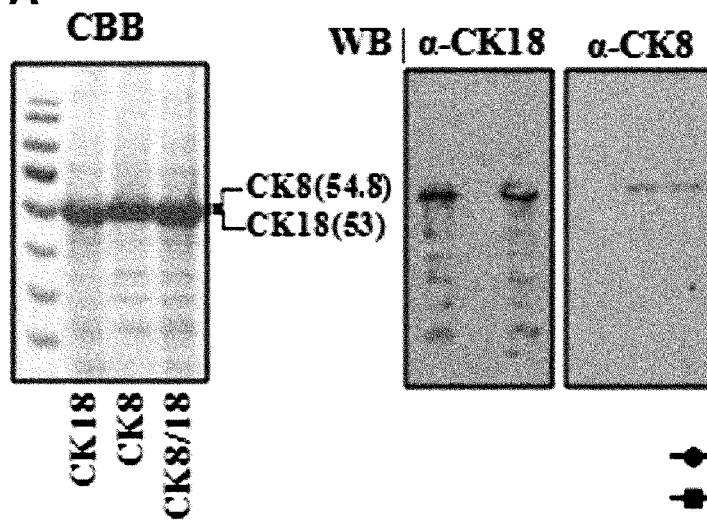
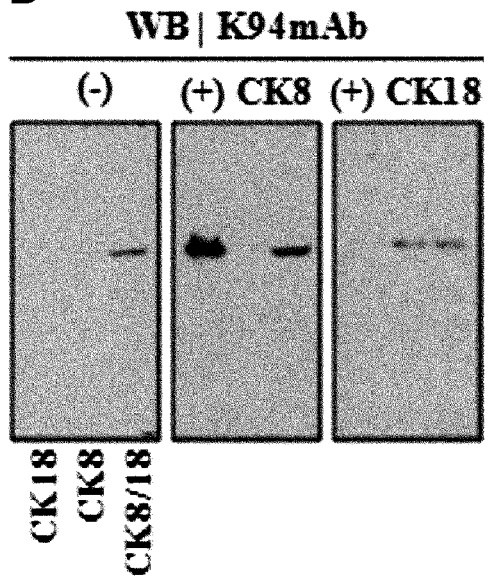
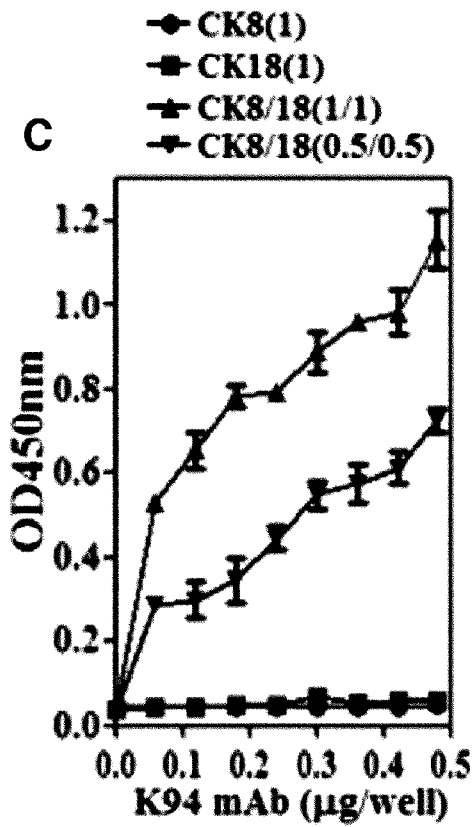

Fig. 11
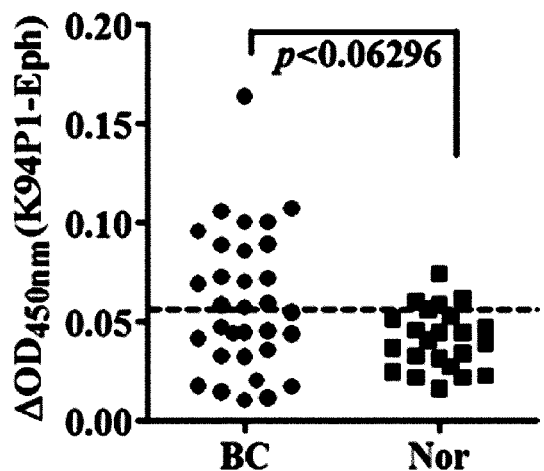
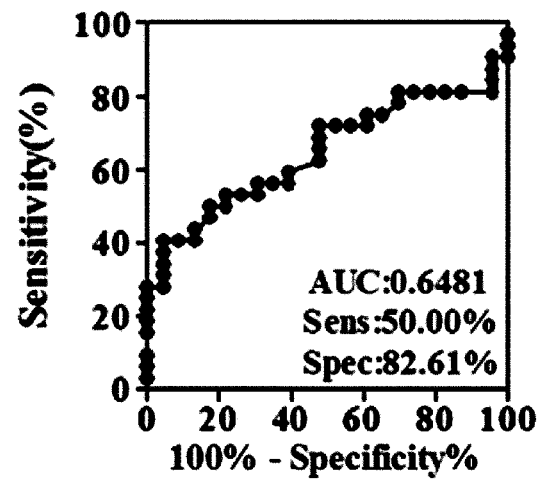
Fig. 12
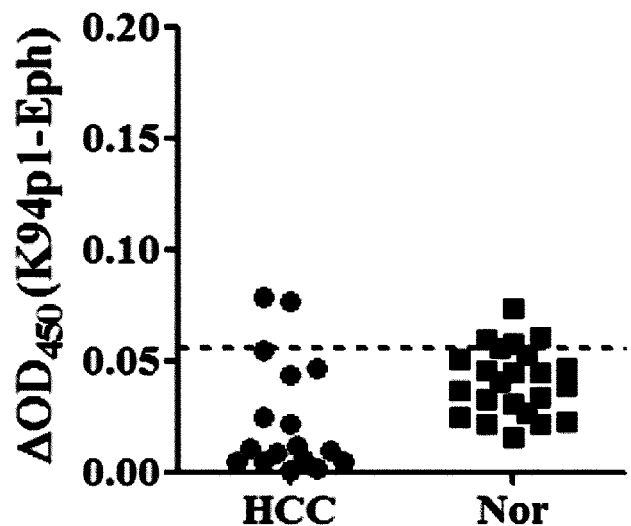

SEQUENCE LISTING

```
<160> NUMBER OF SEQ ID NOS: 35

<210> SEQ ID NO 1
<211> LENGTH: 135
<212> TYPE: PRT
<213> ORGANISM: Artificial Sequence
<220> FEATURE:
<223> OTHER INFORMATION: a heavy chain variable region
<220> FEATURE:
<221> NAME/KEY: UNSURE
<222> LOCATION: (1)
```

<223> OTHER INFORMATION: Any amino acid
<220> FEATURE:
<221> NAME/KEY: UNSURE
<222> LOCATION: (3)
<223> OTHER INFORMATION: Any amino acid
<220> FEATURE:
<221> NAME/KEY: UNSURE
<222> LOCATION: (5)
<223> OTHER INFORMATION: Any amino acid

<400> SEQUENCE: 1

```
Xaa Val Xaa Leu Xaa Gln Ser Gly Pro Gly Ile Leu Gln Pro Ser Gln
  1               5                  10                  15

Thr Leu Ser Leu Thr Cys Ser Phe Ser Gly Phe Ser Leu Ser Thr Phe
             20                  25                  30

Gly Met Gly Val Gly Trp Ile Arg Gln Pro Ser Gly Lys Gly Leu Glu
         35                  40                  45

Trp Leu Ala His Ile Trp Trp Asp Asp Lys Tyr Tyr Asn Pro Ala
 50                  55                  60

Leu Lys Ser Arg Leu Thr Ile Ser Lys Asp Thr Ser Lys Asn Gln Val
 65                  70                  75                  80

Phe Leu Lys Ile Ala Asn Val Asp Thr Ala Asp Thr Ala Thr Tyr Tyr
             85                  90                  95

Cys Ala Arg Ile Gly Gly Tyr Tyr Gly Ser Ser Ser Trp Tyr Phe Asp
            100                 105                 110

Val Trp Gly Thr Gly Thr Thr Val Thr Val Ser Ser Glu Ser Gln Ser
            115                 120                 125

Phe Pro Asn Val Arg Ser Ser
            130                 135
```

<210> SEQ ID NO 2
<211> LENGTH: 115
<212> TYPE: PRT
<213> ORGANISM: Artificial Sequence
<220> FEATURE:
<223> OTHER INFORMATION: a light chain variable region

<400> SEQUENCE: 2

```
Asp Ile Val Ile Thr Gln Thr Pro Ser Ser Leu Ser Ala Ser Leu Gly
  1               5                  10                  15

Gly Lys Val Thr Ile Thr Cys Lys Ala Ser Gln Asp Ile Asn Lys Tyr
             20                  25                  30

Ile Ala Trp Tyr Gln His Lys Pro Gly Lys Gly Pro Arg Leu Leu Ile
         35                  40                  45

His Tyr Thr Ser Thr Leu Gln Pro Gly Ile Pro Ser Arg Phe Ser Gly
 50                  55                  60

Ser Gly Ser Gly Arg Asp Tyr Ser Phe Ser Ile Ser Asn Leu Glu Pro
 65                  70                  75                  80

Glu Asp Ile Ala Thr Tyr Tyr Cys Leu Gln Tyr Asp Asn Leu Leu Thr
             85                  90                  95

Phe Gly Gly Gly Thr Lys Leu Glu Ile Lys Arg Ala Asp Ala Ala Pro
            100                 105                 110

Thr Val Ser
        115
```

<210> SEQ ID NO 3
<211> LENGTH: 12
<212> TYPE: PRT
<213> ORGANISM: Artificial Sequence
<220> FEATURE:

-continued

<223> OTHER INFORMATION: CDR1 of a heavy chain variable region

<400> SEQUENCE: 3

Gly Phe Ser Leu Ser Thr Phe Gly Met Gly Val Gly
1               5                   10

<210> SEQ ID NO 4
<211> LENGTH: 16
<212> TYPE: PRT
<213> ORGANISM: Artificial Sequence
<220> FEATURE:
<223> OTHER INFORMATION: CDR2 of a heavy chain variable region

<400> SEQUENCE: 4

His Ile Trp Trp Asp Asp Lys Tyr Tyr Asn Pro Ala Leu Lys Ser
1               5                   10                  15

<210> SEQ ID NO 5
<211> LENGTH: 14
<212> TYPE: PRT
<213> ORGANISM: Artificial Sequence
<220> FEATURE:
<223> OTHER INFORMATION: CDR3 of a heavy chain variable region

<400> SEQUENCE: 5

Ile Gly Gly Tyr Tyr Gly Ser Ser Ser Trp Tyr Phe Asp Val
1               5                   10

<210> SEQ ID NO 6
<211> LENGTH: 11
<212> TYPE: PRT
<213> ORGANISM: Artificial Sequence
<220> FEATURE:
<223> OTHER INFORMATION: CDR1 of a light chain variable region

<400> SEQUENCE: 6

Lys Ala Ser Gln Asp Ile Asn Lys Tyr Ile Ala
1               5                   10

<210> SEQ ID NO 7
<211> LENGTH: 7
<212> TYPE: PRT
<213> ORGANISM: Artificial Sequence
<220> FEATURE:
<223> OTHER INFORMATION: CDR2 of a light chain variable region

<400> SEQUENCE: 7

Ser Arg Phe Ser Gly Ser Gly
1               5

<210> SEQ ID NO 8
<211> LENGTH: 8
<212> TYPE: PRT
<213> ORGANISM: Artificial Sequence
<220> FEATURE:
<223> OTHER INFORMATION: CDR3 of a light chain variable region

<400> SEQUENCE: 8

Leu Gln Tyr Asp Asn Leu Leu Thr
1               5

<210> SEQ ID NO 9
<211> LENGTH: 405
<212> TYPE: DNA
<213> ORGANISM: Artificial Sequence
<220> FEATURE:
<223> OTHER INFORMATION: a heavy chain variable region

<400> SEQUENCE: 9
saggttmagc tgsagcagtc wggccctggg atattgcagc cctcccagac cctcagtctg    60
acttgttctt tctctgggtt ttcactgagc acttttggta tgggtgtagg ctggattcgt   120
cagccttcag ggaagggtct ggagtggctg gcacacattt ggtgggatga tgataagtac   180
tataacccag ccctgaagag tcggctcaca atctccaagg atacctccaa aaaccaggta   240
ttcctcaaga tcgccaatgt ggacactgca gatactgcca catactactg tgctcgaata   300
ggaggctact acggtagtag ctcctggtac ttcgatgtct ggggcacagg gaccacggtc   360
accgtctcct cagagagtca gtccttccca aatgtcagat cttcc                   405

<210> SEQ ID NO 10
<211> LENGTH: 345
<212> TYPE: DNA
<213> ORGANISM: Artificial Sequence
<220> FEATURE:
<223> OTHER INFORMATION: a light chain variable region

<400> SEQUENCE: 10
gatattgtga tcacacaaac tccatcctca ctgtctgcat ctctggggagg caaagtcacc    60 atcacttgca aggcaagcca agacattaac aagtatatag cttggtacca acacaagcct   120
ggaaaaggtc ctaggctgct catacattac acatctacat tacagccagg catcccatca   180
aggttcagtg gaagtgggtc tgggagagat tattccttca gcatcagcaa cctggagcct   240
gaagatattg caacttatta ttgtctacag tatgataatc ttctcacgtt cggagggggg   300
accaagctgg aaataaaacg gctgatgct gcaccaactg tatcc                    345

<210> SEQ ID NO 11
<211> LENGTH: 36
<212> TYPE: DNA
<213> ORGANISM: Artificial Sequence
<220> FEATURE:
<223> OTHER INFORMATION: CDR1 of a heavy chain variable region

<400> SEQUENCE: 11
gggttttcac tgagcacttt tggtatgggt gtaggc                              36

<210> SEQ ID NO 12
<211> LENGTH: 48
<212> TYPE: DNA
<213> ORGANISM: Artificial Sequence
<220> FEATURE:
<223> OTHER INFORMATION: CDR2 of a heavy chain variable region

<400> SEQUENCE: 12
cacatttggt gggatgatga taagtactat aacccagccc tgaagagt                 48

<210> SEQ ID NO 13
<211> LENGTH: 42
<212> TYPE: DNA
<213> ORGANISM: Artificial Sequence
<220> FEATURE:
<223> OTHER INFORMATION: CDR3 of a heavy chain variable region

<400> SEQUENCE: 13
ataggaggct actacggtag tagctcctgg tacttcgatg tc                       42

<210> SEQ ID NO 14
<211> LENGTH: 33
<212> TYPE: DNA

```
<213> ORGANISM: Artificial Sequence
<220> FEATURE:
<223> OTHER INFORMATION: CDR1 of a light chain variable region

<400> SEQUENCE: 14
aaggcaagcc aagacattaa caagtatata gct                                  33

<210> SEQ ID NO 15
<211> LENGTH: 21
<212> TYPE: DNA
<213> ORGANISM: Artificial Sequence
<220> FEATURE:
<223> OTHER INFORMATION: CDR2 of a light chain variable region

<400> SEQUENCE: 15
tcaaggttca gtggaagtgg g                                               21

<210> SEQ ID NO 16
<211> LENGTH: 24
<212> TYPE: DNA
<213> ORGANISM: Artificial Sequence
<220> FEATURE:
<223> OTHER INFORMATION: CDR3 of a light chain variable region

<400> SEQUENCE: 16
ctacagtatg ataatcttct cacg                                            24

<210> SEQ ID NO 17
<211> LENGTH: 35
<212> TYPE: DNA
<213> ORGANISM: Artificial Sequence
<220> FEATURE:
<223> OTHER INFORMATION: forward primer for mouse heavy chain
<220> FEATURE:
<221> NAME/KEY: misc_difference
<222> LOCATION: (13)
<223> OTHER INFORMATION: g or c-strong interaction (3 hydrogen bonds)
<220> FEATURE:
<221> NAME/KEY: misc_difference
<222> LOCATION: (15)
<223> OTHER INFORMATION: a or g-Purine
<220> FEATURE:
<221> NAME/KEY: misc_difference
<222> LOCATION: (18)
<223> OTHER INFORMATION: g,a,c or t-Any
<220> FEATURE:
<221> NAME/KEY: misc_difference
<222> LOCATION: (19)
<223> OTHER INFORMATION: a or c-Amino
<220> FEATURE:
<221> NAME/KEY: misc_difference
<222> LOCATION: (25)
<223> OTHER INFORMATION: g or c-strong interaction (3 hydrogen bonds)
<220> FEATURE:
<221> NAME/KEY: misc_difference
<222> LOCATION: (28)
<223> OTHER INFORMATION: g or c-strong interaction (3 hydrogen bonds)
<220> FEATURE:
<221> NAME/KEY: misc_difference
<222> LOCATION: (33)
<223> OTHER INFORMATION: a or t-weak interaction (2 hydrogen bonds)

<400> SEQUENCE: 17
cttccggaat tcsargtnma gctgsagsag tcwgg                                35

<210> SEQ ID NO 18
<211> LENGTH: 33
<212> TYPE: DNA
<213> ORGANISM: Artificial Sequence
<220> FEATURE:
<223> OTHER INFORMATION: reverse primer for mouse heavy chain
```

<400> SEQUENCE: 18
ggaagatctg acatttggga aggactgact ctc                     33

<210> SEQ ID NO 19
<211> LENGTH: 32
<212> TYPE: DNA
<213> ORGANISM: Artificial Sequence
<220> FEATURE:
<223> OTHER INFORMATION: forward primer for mouse light chain
<220> FEATURE:
<221> NAME/KEY: misc_difference
<222> LOCATION: (11)
<223> OTHER INFORMATION: c or t-Pyrimidine
<220> FEATURE:
<221> NAME/KEY: misc_difference
<222> LOCATION: (18)
<223> OTHER INFORMATION: a or c-Amino
<220> FEATURE:
<221> NAME/KEY: misc_difference
<222> LOCATION: (20)
<223> OTHER INFORMATION: g or c-strong interaction (3 hydrogen bonds)
<220> FEATURE:
<221> NAME/KEY: misc_difference
<222> LOCATION: (23)
<223> OTHER INFORMATION: a or c-Amino
<220> FEATURE:
<221> NAME/KEY: misc_difference
<222> LOCATION: (26)
<223> OTHER INFORMATION: a or g-Purine
<220> FEATURE:
<221> NAME/KEY: misc_difference
<222> LOCATION: (27)
<223> OTHER INFORMATION: a or t-weak interaction (2 hydrogen bonds)
<220> FEATURE:
<221> NAME/KEY: misc_difference
<222> LOCATION: (30)
<223> OTHER INFORMATION: a or c-Amino

<400> SEQUENCE: 19
gggagctcga yattgtgmts acmcarwctm ca                      32

<210> SEQ ID NO 20
<211> LENGTH: 30
<212> TYPE: DNA
<213> ORGANISM: Artificial Sequence
<220> FEATURE:
<223> OTHER INFORMATION: reverse primer for mouse light chain

<400> SEQUENCE: 20
ggtgcatgcg gatacagttg gtgcagcatc                         30

<210> SEQ ID NO 21
<211> LENGTH: 7
<212> TYPE: PRT
<213> ORGANISM: Artificial Sequence
<220> FEATURE:
<223> OTHER INFORMATION: K94p1

<400> SEQUENCE: 21

Ile Ser Pro Asp Ala His Ser
 1               5

<210> SEQ ID NO 22
<211> LENGTH: 7
<212> TYPE: PRT
<213> ORGANISM: Artificial Sequence
<220> FEATURE:
<223> OTHER INFORMATION: K94p7

<400> SEQUENCE: 22

Thr Leu Ser His Thr Arg Thr
1               5

<210> SEQ ID NO 23
<211> LENGTH: 19
<212> TYPE: RNA
<213> ORGANISM: Artificial Sequence
<220> FEATURE:
<223> OTHER INFORMATION: sense siRNA for CK8

<400> SEQUENCE: 23
ccgcaguuac ggucaacca                                                19

<210> SEQ ID NO 24
<211> LENGTH: 19
<212> TYPE: RNA
<213> ORGANISM: Artificial Sequence
<220> FEATURE:
<223> OTHER INFORMATION: antisense siRNA for CK8

<400> SEQUENCE: 24
ugguugaccg uaacugcgg                                                19

<210> SEQ ID NO 25
<211> LENGTH: 19
<212> TYPE: RNA
<213> ORGANISM: Artificial Sequence
<220> FEATURE:
<223> OTHER INFORMATION: sense siRNA for CK18

<400> SEQUENCE: 25
cucacagagc ugagacgua                                                19

<210> SEQ ID NO 26
<211> LENGTH: 19
<212> TYPE: RNA
<213> ORGANISM: Artificial Sequence
<220> FEATURE:
<223> OTHER INFORMATION: antisense siRNA for CK18

<400> SEQUENCE: 26
uacgucucag cucugugag                                                19

<210> SEQ ID NO 27
<211> LENGTH: 7
<212> TYPE: PRT
<213> ORGANISM: Artificial Sequence
<220> FEATURE:
<223> OTHER INFORMATION: K94p1_D4G

<400> SEQUENCE: 27

Ile Ser Pro Gly Ala His Ser
1               5

<210> SEQ ID NO 28
<211> LENGTH: 7
<212> TYPE: PRT
<213> ORGANISM: Artificial Sequence
<220> FEATURE:
<223> OTHER INFORMATION: K94p1_S2A

<400> SEQUENCE: 28

Ile Ala Pro Asp Ala His Ser
1               5

<210> SEQ ID NO 29
<211> LENGTH: 7
<212> TYPE: PRT
<213> ORGANISM: Artificial Sequence
<220> FEATURE:
<223> OTHER INFORMATION: K94p1_P3A

<400> SEQUENCE: 29

Ile Ser Ala Asp Ala His Ser
 1               5

<210> SEQ ID NO 30
<211> LENGTH: 7
<212> TYPE: PRT
<213> ORGANISM: Artificial Sequence
<220> FEATURE:
<223> OTHER INFORMATION: K94p1_H6A

<400> SEQUENCE: 30

Ile Ser Pro Asp Ala Ala Ser
 1               5

<210> SEQ ID NO 31
<211> LENGTH: 7
<212> TYPE: PRT
<213> ORGANISM: Artificial Sequence
<220> FEATURE:
<223> OTHER INFORMATION: K94p1_S7A

<400> SEQUENCE: 31

Ile Ser Pro Asp Ala His Ala
 1               5

<210> SEQ ID NO 32
<211> LENGTH: 27
<212> TYPE: DNA
<213> ORGANISM: Artificial Sequence
<220> FEATURE:
<223> OTHER INFORMATION: forward primer for human CK8

<400> SEQUENCE: 32
ccgcatatga tgtccatcag ggtgacc                                           27

<210> SEQ ID NO 33
<211> LENGTH: 27
<212> TYPE: DNA
<213> ORGANISM: Artificial Sequence
<220> FEATURE:
<223> OTHER INFORMATION: reverse primer for human CK8

<400> SEQUENCE: 33
atagtcgacc ttgggcagga cgtcaga                                           27

<210> SEQ ID NO 34
<211> LENGTH: 27
<212> TYPE: DNA
<213> ORGANISM: Artificial Sequence
<220> FEATURE:
<223> OTHER INFORMATION: forward primer for human CK18

<400> SEQUENCE: 34
ccggaattca tgagcttcac cactcgc                                           27

<210> SEQ ID NO 35
<211> LENGTH: 27
<212> TYPE: DNA
<213> ORGANISM: Artificial Sequence

```
<220> FEATURE:
<223> OTHER INFORMATION: reverse primer for human CK18

<400> SEQUENCE: 35
atactcgaga tgcctcagaa ctttggt                                              27
```

MARKER COMPRISING ANTI-CK8/18 COMPLEX AUTOANTIBODY AND ITS USE FOR DIAGNOSING CANCER

RELATED APPLICATIONS

This application is a National Phase of PCT Patent Application No. PCT/KR2012/001264 having International filing date of Feb. 20, 2012, which claims the benefit of priority of Korean Patent Application Nos. 10-2011-0014809 filed on Feb. 18, 2011 and 10-2012-0011503 filed on Feb. 3, 2012. The contents of the above applications are all incorporated by reference as if fully set forth herein in their entirety.

SEQUENCE LISTING STATEMENT

The ASCII file, entitled 57291SequenceListing.txt, created on Aug. 14, 2013, comprising 10,637 bytes, submitted concurrently with the filing of this application is incorporated herein by reference.

FIELD AND BACKGROUND OF THE INVENTION

The present invention relates to a cytokeratin 8/18 complex-specific autoantibody or a fragment comprising an antigen-binding site (paratope) thereof, use thereof in the diagnosis of breast cancer, a polypeptide having an amino acid sequence of an epitope specifically binding to the autoantibody, a composition for diagnosing breast cancer comprising an agent capable of measuring an expression level of the autoantibody or the fragment comprising an antigen-binding site thereof, a hybridoma cell line producing the autoantibody, and a kit for diagnosing breast cancer comprising the composition of the present invention. Further, the present invention relates to a method for diagnosing breast cancer, comprising the step of detecting the cytokeratin 8/18 complex-specific autoantibody or the fragment comprising the antigen-binding site thereof using the composition of the present invention, and a method for screening a therapeutic agent for breast cancer using the autoantibody.

Breast cancer has the highest incidence rates among various cancers in most OECD countries. In Korea, the incidence has also been increasing, concurrent with rising prevalence of obesity and the Westernization of dietary habits. Diagnosis of breast cancer is usually made by mammography, ultrasonography, and Magnetic Resonance imaging (MRI). Mammography is an X-ray examination of the compressed breast, and is useful for detection of small breast cancers. However, many Korean women have less fatty tissue and denser fibrous tissue, and thus it is difficult to detect calcification as an early warning sign of breast cancer. Therefore, a mammogram is usually performed together with ultrasonography which is useful for the detection of solid and cystic breast masses. These mechanical examinations are conducted by a simple examination procedure, but have limited detection accuracy because they rely on a reader's subjective interpretation. Therefore, subsequent tissue biopsy is required. Such tissue biopsy is an invasive method including examination of breast cancer-specific protein expression in the tissue or tissue observation, and requires considerable costs while imposing emotional, physical, and economic burdens on patients. In order to overcome these drawbacks, there is a need to develop an easy and simple diagnostic method for breast cancer.

Meanwhile, the immune system is constructed as a peculiar system distinguishing the self from non-self at an early stage of development, and develops to induce antigen-antibody reaction (humoral immune response) and cellular immune response against foreign antigens only which are exposed to the immune system under normal conditions. However, the generation of antibodies against self-antigens was observed in specific diseases, which is attributed to extracellular release of intracellular antigens due to abnormal expression site of the corresponding antigens, modification of forms, or other aberrant characteristics. Since the 1970s, it has been also reported that the generation of autoantibodies against cancer cell-derived antigens is observed in carcinogenesis, accompanied by abnormal tumor growth, and they are called tumor-associated antigens and tumor-associated autoantibodies. Autoantibodies generated by tumor-associated antigens pre-exist and are found before the onset of disease, suggesting the availability as a biomarker for the early diagnosis.

Until now, various tumor-associated antigens have been identified. Among them, overexpression of HER-2/neu oncoprotein found in 20-30% of breast cancer patients is known to induce autoantibodies, and a tumor suppressor protein p53 is also reported to induce autoantibodies. The cell proliferation-associated proteins, cyclin B1 and CENP-F (centromere protein F) are also known to induce autoantibodies. These results suggest the presence of autoantibodies against a larger number of tumor-associated antigens, and many trials have been made to screen tumor-associated autoantibodies that can be utilized as a cancer biomarker.

For identification of tumor-associated autoantibodies, SEREX (selological analysis of recombinant cDNA expression libraries of human tumors with autologous serum), which is a conventional method of searching autoantibodies by analyzing reactivity of cancer patient sera with cancer cell-derived gene expression libraries, has been used. However, it is difficult to express cancer cell-derived proteins with maximal diversity at the library level. In addition, even after transcription, final protein products undergo posttranslational modification (PTM) such as phosphorylation and glycosylation, which is not reflected in the protein expression libraries. Therefore, the method is not sufficient to detect autoantigens. Alternatively, proteomics-based identification of autoantibodies has been recently conducted. The proteomics-based method includes the procedures of performing two-dimensional polyacrylamide gel electrophoresis (2D-PAGE) of cancer cell-derived proteins, detecting protein spots showing reactivity using cancer patient serum as an autoantibody sample, and identifying the proteins by mass spectrometry, and is commonly abbreviated to SERPA (serological proteome analysis). MAPPING (multiple affinity protein profiling) is also used, in which an affinity chromatography resin is conjugated with antibodies isolated from the patient blood, and cancer cell-derived proteins are applied thereto to identify binding proteins by mass; spectrometry. In addition, cancer cell lysates are separated into several thousand individual fractions to fabricate a protein chip, and the reactivity of patient blood thereto is examined to identify autoantibodies. Such various proteomics-based identification methods are advantageous in that the reactivity of antibodies against cancer cell-derived proteins with posttranslational modifications (PTM) can be directly examined, and thus are able to identify autoantibodies that cannot be identified by SEREX.

However, the above methods still include other limitations. First, there is a problem in the quantity of antibodies. When an analyte is a mixture of two or more components, a relatively large amount of the analyte takes precedence over other analyte in the analysis. This means that minorities are possibly excluded from the analyzable range. In this context, a patient's serum is a mixture of numerous antibodies, an analytically measurable range is determined by the differences in quantity of the constituting autoantibodies and their affinity for antigens, and therefore analysis on the desired autoantibodies could be impractical. Second, due to the dependence of the autoantibody samples to be analyzed on a patient, there is a limitation in the systematic analysis of autoantibody production according to carcinogenesis, and there is also difficulty in collecting a large enough amount of blood samples from patients, which becomes an obstacle to further studies. Finally, there is a problem in the preservation of epitopes reacting with antibodies. According to the current immunological knowledge, there are two types of epitopes, sequential epitopes and conformational epitopes. In vivo induction of antigen-specific antibody production reflects an antigen being encountered by the immune cell antibody for the first time, which means that the antigen-antibody reaction occurs in a solution, and the antigen protein has a structure of maintaining its solubilized form in the blood. Thus, ex vivo test of antigen-antibody reaction is preferably performed in the solution, because their natural binding pattern is well reflected in the solution. In the above mentioned SERPA, however, two-dimensional electrophoresis is performed for the analysis of a protein mixture. That is, proteins to be analyzed are denatured by using SDS and urea, and then their reaction with antibodies is examined. Thus, if the epitope is a sequential epitope, it is detectable, but if the epitope is a conformational epitope, not detectable.

Although the previous studies on autoantibodies suggested their availability as a carcinogenesis-associated maker, their diagnostic effects are not satisfactory, and there is still a limitation in the availability of autoantibodies as a biomarkers for cancer diagnosis. Further, the autoantibody detection methods have limitations in practical application because they do not include a large number of cases or do require excessive experiments. Actually, there are still difficulties in the identification of autoantibodies as a diagnostic marker for cancer.

SUMMARY OF THE INVENTION

Hence, the present inventors have made an effort to develop autoantibodies for the diagnosis of breast cancer. As a result, they developed a method for identifying effective tumor-associated autoantibodies using a tumor model mouse, and found that autoantibodies against cytokeratin 8/18 complex are induced in the tumor model mouse. Further, the present inventors screened a phage expressing an antigenic determinant (epitope) specifically binding thereto from a peptide library so as to design an ELISA for the autoantibody detection, and they found that an individual with breast cancer can be diagnosed using the same, thereby completing the present invention.

An object of the present invention is to provide a cytokeratin 8/18 complex-specific autoantibody or a fragment comprising an antigen-binding site thereof.

Another object of the present invention is to provide a polypeptide which is an epitope specifically binding to the autoantibody of the present invention.

Still another object of the present invention is to provide a composition for diagnosing breast cancer, comprising an agent capable of measuring an expression level of the autoantibody of the present invention or the fragment comprising an antigen-binding site thereof.

Still another object of the present invention is to provide a hybridoma cell line producing the autoantibody of the present invention.

Still another object of the present invention is to provide a kit for diagnosing breast cancer comprising the composition of the present invention.

Still another object of the present invention is to provide a method for diagnosing breast cancer, comprising the step of detecting the cytokeratin 8/18 complex-specific autoantibody or the fragment comprising the antigen-binding site thereof using the composition of the present invention.

Still another object of the present invention is to provide a method for screening a therapeutic agent for breast cancer, comprising the steps of (a) measuring the expression level of the cytokeratin 8/18 complex-specific autoantibody; (b) administering a candidate therapeutic agent for breast cancer; and (c) examining whether the expression level of the cytokeratin 8/18 complex-specific autoantibody is reduced, compared to that in step (a).

Still another object of the present invention is to provide use of the autoantibody of the present invention or the fragment comprising an antigen-binding site thereof in the diagnosis of breast cancer.

When the cytokeratin 8/18 complex-specific autoantibody of the present invention is used as a diagnostic marker for breast cancer, the incidence of breast cancer can be diagnosed with 50% sensitivity and 82% specificity using non-invasive biological samples such as blood, plasma, serum, and lymphatic fluid without using an invasive tissue sample. Furthermore, a sequence reacting with the marker is identified in the present invention. Therefore, it is not necessary to design a complex reacting substance for marker identification, and breast cancer can be diagnosed by using only the identified amino acid sequence, leading to the development of a diagnostic kit for breast cancer.

BRIEF DESCRIPTION OF THE DRAWINGS

FIG. 3 shows the reactivity of TAB-K94 antibody to various cancer cell lines and the result of immunohistostaining of human cancer tissues. (A) shows the reactivity measured by flow cytometry after intracellular staining of various cancer cells with TAB-K94 antibody. High reactivity was observed in the liver cancer cell line HepG2 and the breast cancer cell line MCF-7, whereas lower reactivity was observed in normal cell lines, Chang liver cells and HT22 neuronal cells. (B) is the result of immunohistochemistry showing the reactivity of TAB-K94 antibody to human cancer tissues. Because of a high non-specific reactivity, hardly any distinct reaction was observed in the liver cancer tissues (data not shown), but a strong complete staining by reaction with TAB-K94 antibody was observed in the breast cancer tissues, in particular, at the invasive front.

FIGS. 4a-b show the result of analyzing complementarity determining regions (CDRs) of the heavy chain variable region (VH) and the light chain variable region (VL) of TAB-K94 antibody. Total RNA was extracted from TAB-K94 antibody-producing B cell hybridoma to synthesize cDNA, PCR for amplification was performed using primers for complementarity determining regions of the heavy chain variable region and light chain variable region, and the amplified product was ligated into a pTOP Blunt V2 vector to prepare a recombinant plasmid. The recombinant plasmid was amplified in a host cell, and extracted, and the corresponding region was analyzed by sequencing. The protein sequence was analyzed from the identified base sequence, and the CDR sequence was determined according to Kabat CDR definition.

FIG. 5 shows the results of Western blotting for analysis of TAB-K94 antibody-specific antigen protein and in-gel digestion for identification of the corresponding protein. Cell lysate (CL) of various cancer cell lines and serum-free cell culture medium (CCM) were quantified, each 50 µg thereof was run on 10% (w/v) SDS-PAGE, and then Western blotting was performed using TAB-K94 antibody (A). As a result, very high reactivity was observed in not only cell lysate but cell culture medium of the breast cancer cell line MCF-7. On the basis of this, the MCF-7 cell culture medium was used for the identification of TAB-K94 antibody-specific antigen. An excessive amount of cell culture medium was collected, and concentrated, followed by fractionation using a HiTrap-Q ion exchange resin chromatography. A fraction containing TAB-K94 antibody-specific antigen was only collected, concentrated, and run on 8 to 10% (w/v) SDS-PAGE. A part thereof was used for Western blotting to examine the presence of TAB-K94 antigens, and the rest was used for coomassie staining to examine the protein bands. Two protein bands corresponding to the TAB-K94 antibody reaction were used for protein identification by mass spectrometry (B).

FIG. 7 is the result showing that the TAB-K94 antibody is an antibody against CK8/18 complex identified via examination using recombinant proteins. In order to examine the reactivity of TAB-K94 antibody to CK8 and CK18 confirmed by the protein identification, CK8 (MW: 54.8 kDa, tag sequence included) and CK18 (MW: 53 kDa, tag sequence included) recombinant proteins were prepared. In (A), the recombinant proteins were analyzed on SDS-PAGE by coomassie staining, and expression of the correct recombinant proteins was examined by using antibodies (CK8-specific or CK18-specific antibody) specific to each protein. (B) is the result of Western blotting in order to examine the reactivity of each protein confirmed above or a mixture thereof to TAB-K94 antibody. As a result, when CK8 or CK18 was run alone, TAB-K94 antibody reaction was not observed, but when the CK8/18 mixture was run, the react ion was observed. In (C), in order to confirm that the reactivity to TAB-K94 antibody was only showed when CK8 and CK18 formed a protein complex, it was shown that its reactivity to TAB-K94 antibody was induced in the case of treatment of CK18 or CK8 protein to PVDF membrane before reacting TAB-K94 antibody. ELISA of CK8, CK18 or CK8/18 mixture was performed for the analysis.

FIG. 11 shows the result of analyzing the sera of breast cancer patients and normal individuals using the selected K94p1. (A) is the result of ELISA analyzing the sera of breast cancer patients and normal individuals using K94p1, which is a phage expressing TAB-K94 antibody-specific peptide, as a coating antigen. As a result, when the cutoff value was determined as 0.056, breast cancer patients can be diagnosed with 50% sensitivity and 82.61% specificity, which is shown in (B).

FIG. 12 is the result of analyzing the sera of liver cancer patients and normal individuals using the selected K94p1. ELISA was performed using K94p1, which is a phage expressing TAB-K94 antibody-specific peptide, as a coating antigen, so as to analyze the sera of liver cancer patients and normal individuals. As a result, there was no significant difference between the sera of liver cancer patients and normal individuals, unlike that in breast cancer.

DESCRIPTION OF SPECIFIC EMBODIMENTS OF THE INVENTION

Figure 1:
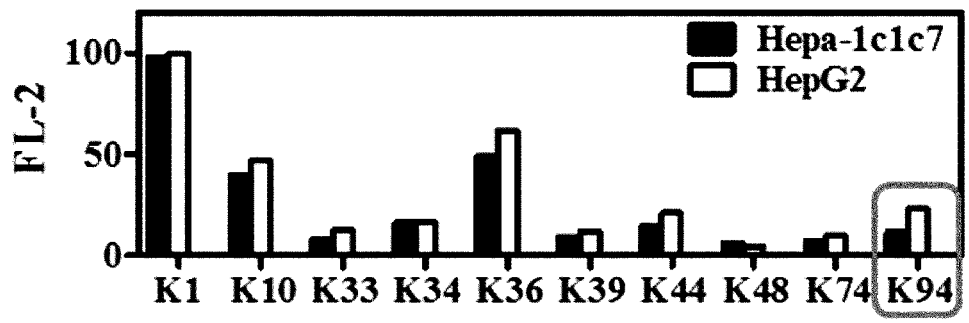
FIG. 1 shows the reactivity of autoantibodies obtained from B cell hybridoma clones derived from H-ras12V liver cancer transgenic mice to liver cancer cells. From the above results, TAB-K94 antibodies were obtained. Specifically, after fixation & permeabilization, the liver cancer cell lines HepG2 and Hepa1c1c7 were treated with the liver cancer model mice-derived autoantibodies, and reacted with a secondary antibody labeled with a fluorescent substance, followed by flow cytometry.

In one embodiment to achieve the above objects, the present invention provides a cytokeratin 8/18 complex-specific autoantibody or a fragment including an antigen-binding site thereof.

As used herein, the term "cytokeratin (CK)" is one of the intermediate filaments, and means a filament mainly found in epithelial cells. CK is an essential component that forms the cytoskeleton, and it maintains intact cell shape and fixes the nucleus. Total 20 different subtypes exist. CK expression is related to the degree of maturation or differentiation within various epithelia in the human body, and the CK isotype depends on the cell type and the localization of CK in the cytoplasm. The different CK types depend on whether they are acidic or basic types, as well as molecular weight, and the distribution of the various CKs differs between the several kinds of epithelia throughout the entire human body.

As used herein, the term "cytokeratin 8/18 complex" means a complex of cytokeratin 8 and its complementary subunit cytokeratin 18. In normal tissues, cytokeratin 8 or cytokeratin 18 is mainly expressed in the glandular or transitional epithelial cells and liver cells, whereas its expression is often reduced in breast cancer and colon cancer, and increased in head and neck cancer. Its expression is reported to induce cancer progression and poor prognosis. However, autoantibodies against cytokeratin 8 or cytokeratin 18 have not been found in the sera of breast cancer patients, and the present inventors first developed the cytokeratin 8/18-specific autoantibody and demonstrated that it can be used for the diagnosis of breast cancer.

As used herein, the term "autoantibody" means an antibody specifically reacting with a self-protein. The body does not usually start an immune response against its own antigens, and thus does not produce antibodies. Occasionally, the body recognizes its own protein as an antigen to produce an antibody, leading to autoimmune diseases such as systemic lupus erythematosus and rheumatoid arthritis. On the other hand, the autoantibody of the present invention means an antibody against cancer cell-associated antigens accompanied by abnormal tumor growth. Specifically, the autoantibody of the present invention means an antibody against a tumor-associated antigen, cytokeratin 8/18 complex.

In the present invention, an antigen-binding site of the autoantibody against cytokeratin 8/18 complex highly expressed in the breast cancer tissue was identified, and the corresponding antibody was designated as 'TAB-K94 antibody', 'TAB-K94 autoantibody' or 'autoantibody TAB-K94'. In order to study the characteristics of the autoantibody, the present inventors performed sequencing analysis of the autoantibody of the present invention. As a result, it was found that the autoantibody of the present invention includes a heavy chain variable region including a heavy chain CDR1 represented by SEQ ID NO. 3; a heavy chain CDR2 represented by SEQ ID NO. 4; and a heavy chain CDR3 represented by SEQ ID NO. 5, and a light chain variable region including a light chain CDR1 represented by SEQ ID NO. 6; a light chain CDR2 represented by SEQ ID NO. 7; and a light chain CDR3 represented by SEQ ID NO. 8, and includes a heavy chain amino acid sequence represented by SEQ ID NO. 1 and a light chain amino acid sequence represented by SEQ ID NO. 2. In general, a single antibody molecule has two heavy chains and two light chains, and each heavy chain and light chain includes a variable region at its N-terminus. Each variable region is composed of three complementarity determining regions (CDR) and four framework regions (FRs), and complementarity determining regions determine the antigen binding specificity of antibody, and exist as a relatively short peptide sequence supported by conserved framework regions within the variable domains. Preferably, the autoantibody of the present invention may include an autoantibody that is composed of the CDR1 sequence of SEQ ID NO. 3, the CDR2 sequence of SEQ ID NO. 4 or the CDR3 sequence of SEQ ID NO. 5, or a fragment including an antigen-binding site thereof, as a part of the heavy chain variable region, and it may be an autoantibody including all of the CDR1, CDR2 and CDR3 sequences or a fragment thereof. Further, the autoantibody of the present invention may include an autoantibody that is composed of the CDR1 sequence of SEQ ID NO. 6, the CDR2 sequence of SEQ ID NO. 7 or the CDR3 sequence of SEQ ID NO. 8, or a fragment including an antigen-binding site thereof, as a part of the light chain variable region. Furthermore, it is apparent that nucleic acid sequences encoding the sequences are also included in the present invention.

More preferably, the autoantibody of the present invention may include an autoantibody consisting of the amino acid sequence of SEQ ID NO. 1, or a fragment including an antigen-binding site thereof, as a heavy chain variable region sequence, and an autoantibody consisting of the amino acid sequence of SEQ ID NO. 2, or a fragment including an antigen-binding site thereof, as a light chain variable region sequence. Further, the heavy chain and the light chain may be used singly or together depending on the purpose, and any combinations of a plurality of CDR sequences and light chain and heavy chain are possible according to the typical genetic engineering method depending on the purpose of those skilled in the art.

There is no report on the formation of autoantibodies against the cytokeratin 8/18 complex in breast cancer. In particular, the present inventor investigated for the first time a significant increase of autoantibodies against the cytokeratin 8/18 complex in an individual with breast cancer, leading to identification of a peptidomimetic sequence of the epitope of the cytokeratin 8/18 complex.

The autoantibody of the present invention includes a polynucleotide encoding two full-length heavy chains or a fragment having an immunological activity of the antibody molecule to achieve antibody-antigen binding. Further, the autoantibody of the present invention includes a polynucleotide encoding two full-length light chains or a fragment having an immunological activity of the antibody molecule to achieve antibody-antigen binding. The fragment having an immunological activity of the antibody molecule indicates a fragment retaining antigen-binding capacity, and examples of the antibody fragment include (i) the Fab fragment consisting of a light chain variable region (VL), a heavy chain variable region (VH), a light chain constant region (CL) and a heavy chain constant region 1 (CH1); (ii) the Fd fragment consisting of the VH and CH1 domains; (iii) the Fv fragment consisting of the VL and VH domains of a monoclonal antibody; (iv) the dAb fragment (Ward E S et al., Nature 341:544-546 (1989)] which consists of a VH domain; (v) isolated CDR regions; (vi) F(ab')2 fragments, a bivalent fragment including two linked Fab fragments; (vii) single chain Fv molecules (scFv), in which a VH domain and a VL domain are linked by a peptide linker which allows the two domains to be connected to form an antigen binding site; (viii) bispecific single chain Fv dimers (PCT/US92/09965) and (ix) "diabodies", multivalent or multispecific fragments constructed by gene fusion (WO94/13804), but are not limited thereto. Preferably, the autoantibody of the present invention or the fragment including an antigen-binding site thereof may be an autoantibody or a fragment including an antigen-binding site thereof produced by a hybridoma cell line of Accession No. KCTC 11799BP, more preferably an autoantibody or a fragment including an antigen-binding site thereof recognizing the amino acid sequence of ISPDAHS (Ile-Ser-Pro-Asp-Ala-His-Ser) represented by SEQ ID NO. 21, TLSHTRT (Thr-Leu-Ser-His-Thr-Arg-Thr) represented by SEQ ID NO. 22, ISPGAHS (Ile-Ser-Pro-Gly-Ala-His-Ser) represented by SEQ ID NO. 27, IAPDAHS (Ile-Ala-Pro-Asp-Ala-His-Ser) represented by SEQ ID NO. 28, ISADAHS (Ile-Ser-Ala-Asp-Ala-His-Ser) represented by SEQ ID NO. 29, ISPDAAS (Ile-Ser-Pro-Asp-Ala-Ala-Ser) represented by SEQ ID NO. 30, or ISPDAHA (Ile-Ser-Pro-Asp-Ala-His-Ala) represented by SEQ ID NO. 31 that is an epitope, and most preferably an autoantibody or a fragment including an antigen-binding site thereof recognizing the amino acid sequence of ISPDAHS represented by SEQ ID NO. 21, IAPDAHS represented by SEQ ID NO. 28 or ISPDAHA represented by SEQ ID NO. 31, wherein I represents isoleucine (Ile), S does serine (Ser), P does proline (Pro), D does aspartic acid (Asp), A does alanine (Ala), H does histidine (His), T does threonine (Thr), L does leucine (Leu), R does arginine (Arg), and G does glycine (Gly) among 20 essential amino acids.

In order to identify an epitope sequence binding to the autoantibody of the present invention, the present inventors utilized a phage-display cyclic peptide library system forming a cyclic structure by 7 amino acids. Preferably, phages specifically binding to cytokeratin 8/18 complex-specific autoantibody are selected. From the selected phages, phage groups showing high reactivity to cytokeratin 8/18 complex-specific autoantibody of the present invention are only purified and employed as coating antigens, and then reactivity of antibodies to the antigens was examined to analyze their amino acid sequence.

In another embodiment, the present invention provides a polypeptide having the amino acid sequence of ISPDAHS represented by SEQ ID NO. 21, TLSHTRT represented by SEQ ID NO. 22, ISPGAHS represented by SEQ ID NO. 27, IAPDAHS represented by SEQ ID NO. 28, ISADAHS represented by SEQ ID NO. 29, ISPDAAS represented by SEQ ID NO. 30, or ISPDAHA represented by SEQ ID NO. 31, which is an epitope specifically binding to the autoantibody of the present invention.

Preferably, polypeptides consisting of the seven amino acids are prepared to include additional cysteines (Cys; C) at both ends in the form of CX7C, and thus they are able to form a stable cyclic structure. Such polypeptides can be used as an epitope-mimetic peptide detecting the autoantibody of the present invention. In the specific Example of the present invention, a phage expressing cyclic peptide library (Ph.D.-C7C Phage Display Peptide Library kit; New England Biolabs), where 7 amino acids having cysteines at both ends form a cyclic structure, was used to identify ISPDAHS represented by SEQ ID NO. 21 showing high reactivity to TAB-K94 antibody from random sequences (Table 2). Furthermore, each amino acid residue of the sequences is substituted with glycine or alanine to examine its reactivity, so as to identify epitope-mimetic polypeptides represented by SEQ ID NOs. 27 to 31, which maintain the antibody reactivity partially or nearly as it is (Table 3).

In still another embodiment, the present invention provides a composition for diagnosing breast cancer, comprising an agent capable of measuring an expression level of the autoantibody of the present invention or the fragment comprising an antigen-binding site thereof.

As used herein, the term "diagnosis" refers to evaluation of the presence or properties of pathological states. With respect to the objects of the present invention, diagnosis includes not only the determination of the incidence of breast cancer but also the prediction of the outcomes of the treatment, including recurrence, metastatic spread, and drug reactivity and resistance. Preferably, the autoantibody against cytokeratin 8/18 complex of the present invention is used to determine the expression level of cytokeratin 8/18 in a sample isolated from an individual suspected of having breast cancer, thereby predicting the prognosis of the individual as well as diagnosing the incidence of breast cancer. Preferably, the autoantibody may be an antibody specifically recognizing the amino acid sequence of ISPDAHS represented by SEQ ID NO. 21, IAPDAHS represented by SEQ ID NO. 28, or ISPDAHA represented by SEQ ID NO. 31, but is not limited thereto.

As used herein, the term "sample isolated from an individual" refers to a tissue, a cell, whole blood, serum, plasma, saliva, sputum, cerebrospinal fluid or urine that shows a difference in the expression levels of cytokeratin 8/18 complex, but is not limited thereto.

As used herein, the term "diagnostic marker, marker for diagnosis, or diagnosis marker", is intended to indicate a substance capable of diagnosing cancer by distinguishing cancer cells from normal cells. Preferably, the diagnostic marker of the present invention may be an autoantibody specifically binding to cytokeratin 8/18 complex for the diagnosis of breast cancer. In the Examples of the present invention, the composition of the present invention is used to perform the immunohistochemical staining of breast cancer tissues. As a result, the composition was found to specifically stain the cytokeratin 8/18 complex overexpressed only in breast cancer, and in particular, the reaction with the composition including the autoantibody of the present invention was prominent in the invasive front region of breast cancer tissue (FIG. 3B).

As used herein, the term "breast cancer" refers to a malignant tumor that has developed from cells in the breast, and usually means a cancer developed in the ducts and the lobules of the breast. The risk factors of breast cancer are not yet clarified, but factors such as estrogen, age, experience of birth, alcohol consumption, and family history are associated with an increased risk of breast cancer. Reportedly, the 5-year survival rate of stage 0 breast cancer is as high as 100%, but that of stage 4 breast cancer is lower than 20%. There are treatment options of surgery, chemotherapy, radiation, and hormonal therapy. Thus, early diagnosis is the most important. Accordingly, the present inventors confirmed that the autoantibody of the present invention is used to diagnose the incidence of breast cancer with high specificity (FIGS. 11 and 12). The conventional methods which detect proteins overexpressed in cancer are not suitable for diagnosing cancer because of reduced half-life of tumor-specific protein released into the blood. Thus, it is problematic for use as a diagnostic marker for cancer. The autoantibody against cytokeratin 8/18 complex of the present invention has a long half-life showing high detection sensitivity and samples like blood can be also simply collected from patients by a non-invasive method. Thus, the autoantibody of the present invention is suitably used as a diagnostic marker for cancer.

As used herein, the term "agent capable of measuring an expression level of cytokeratin 8/18 complex-specific autoantibody" means a molecule that is used for the detection of the marker by measuring the expression level of cytokeratin 8/18 complex-specific autoantibody, a marker, overexpressed in the whole blood, serum, plasma, lymphatic fluid and interstitial fluid of individuals with breast cancer or suspected of having breast cancer. Preferably, it may be a polypeptide specifically binding to the autoantibody. The polypeptide specifically binding to the autoantibody may be a polypeptide having the amino acid sequence of ISPDAHS represented by SEQ ID NO. 21, TLSHTRT represented by SEQ ID NO. 22, ISPGAHS represented by SEQ ID NO. 27, IAPDAHS represented by SEQ ID NO. 28, ISADAHS represented by SEQ ID NO. 29, ISPDAAS represented by SEQ ID NO. 30, or ISPDAHA represented by SEQ ID NO. 31. The polypeptides may be prepared to have a stable cyclic structure by addition of cysteines at both ends, and also prepared in the form of a fusion protein with a carrier protein in order to acquire an effective expression construct of the epitope. As used herein, the term "carrier protein" means a protein or a fragment thereof that binds with a desired protein or polypeptide to effectively maintain the expression of an epitope. It may be GFP (green fluorescence protein), HSA (human serum albumin), or MBP (maltose binding protein), but is not limited thereto, and is preferably MBP. In the specific Example of the present invention, MBP showing no non-specific binding to human serum is used as the carrier protein to prepare the polypeptide of the present invention in the form of fusion protein, in order to increase sensitivity and specificity of the diagnostic kit (Example 13).

Analysis methods for measuring the expression levels include, but are not limited to, Western blotting, ELISA (Enzyme Linked Immunosorbent Assay), radioimmunoassay (otA), radioimmunodiffusion, Ouchterlony immunodiffusion, rocket immunoelectrophoresis, immunohistostaining, immunoprecipitation assay, complement fixation assay, FACS, and protein chip assay. By the above detection methods, formation of antigen-antibody complex in normal control samples can be compared with that in individuals with breast cancer or suspected of having the breast cancer, thereby diagnosing the incidence of breast cancer in patients suspected of having breast cancer.

The diagnostic method for breast cancer may be achieved by an antibody-antigen reaction between the cytokeratin 8/18 complex-specific autoantibody of the present invention and the antigen specifically binding thereto. As used herein, the term "antigen-antibody complex" is intended to refer to a binding product of the breast cancer marker autoantibody to an antigen specific thereto. The amount of formed antigen-antibody complexes may be quantitatively determined by measuring the signal intensity of a detection label. Preferably, the antigen-antibody complex in the present invention may be a binding product of the cytokeratin 8/18 complex-specific antibody and the antigen specific thereto.

Such a detection label may be selected from the group consisting of enzymes, fluorescent substances, ligands, luminescent substances, microparticles, redox molecules and radioactive isotopes, but the present invention is not limited to the examples. Examples of enzymes available as detection labels include, but are not limited to, β-glucuronidase, β-D-glucosidase, β-D-galactosidase, urase, peroxidase or alkaline phosphatase, acetylcholinesterase, glucose oxidase, hexokinase and GDPase, RNase, glucose oxidase and luciferase, phosphofructokinase, phosphoenolpyruvate carboxylase, aspartate aminotransferase, phosphoenolpyruvate decarboxylase, and β-latamase. Examples of the fluorescent substances include, but are not limited to, fluorescein, isothiocyanate, rhodamine, phycoerythrin, phycocyanin, allophycocyanin, o-phthaldehyde and fluorescamine. Examples of the ligands include, but are not limited to, biotin derivatives. Examples of luminescent substances include, but are not limited to, acridinium esters, luciferin and luciferase. Examples of the microparticles include, but are not limited to, colloidal gold and colored latex. Examples of the redox molecules include, but are not limited to, ferrocene, ruthenium complexes, viologen, quinone, Ti ions, Cs ions, diimide, 1,4-benzoquinone, hydroquinone, $K_4W(CN)_8$, $[Os(bpy)_3]^{2+}$, $[RU(bpy)_3]^{2+}$, and $[MO(CN)_8]^{4-}$. Examples of the radioactive isotopes include, but are not limited to, $^3H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$.

Further, the present inventors demonstrated that the medium body specifically binding to a CK8/18 complex can be used as a diagnostic marker for breast cancer by the following experiment.

First, spleen cells were obtained from a liver cancer mouse model as a parental cell, and fused with myeloma cells to produce B cell hybridomas. From the antibodies secreted by the produced hybridoma cells, antibodies showing reactivity with liver cancer cells were selected to isolate the TAB-K94 autoantibody of the present invention (FIG. 1).

Figure 2:
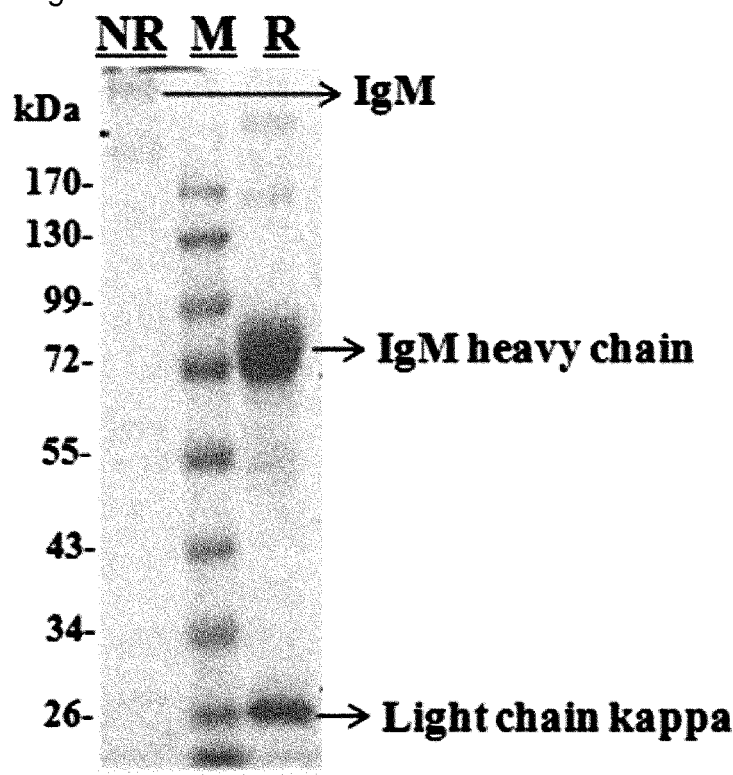
FIG. 2 shows the result of SDS-PAGE electrophoresis of the purified TAB-K94 antibody. The IgM-type TAB-K94 antibody was purified using MBP-agarose or protein L-agarose, and 10 μg of the purified antibody was treated with sample solutions treated with a reducing agent (R) or no reducing agent (NR), and run on 10% SDS-electrophoresis gel, followed by coomassie staining. When it was not treated with the reducing agent, IgM was found to have a molecular weight of 170 kDa or higher. When it was treated with the reducing agent, heavy chain and light chain proteins were found to have molecular weights of 72 kDa and 25 kDa, respectively.

Thereafter, the presence of antigen reacting with the isolated autoantibody was examined. For more specific analysis of the antigen, the isolated autoantibody TAB-K94 was purified in a large amount, and MBP-agarose (mannose binding protein-agarose) or protein L-agarose purification was performed to examine the intracellular expression site of the antigen (expression in the cell membrane) and identify the corresponding autoantigen proteins (FIG. 2).

Figure 6C:
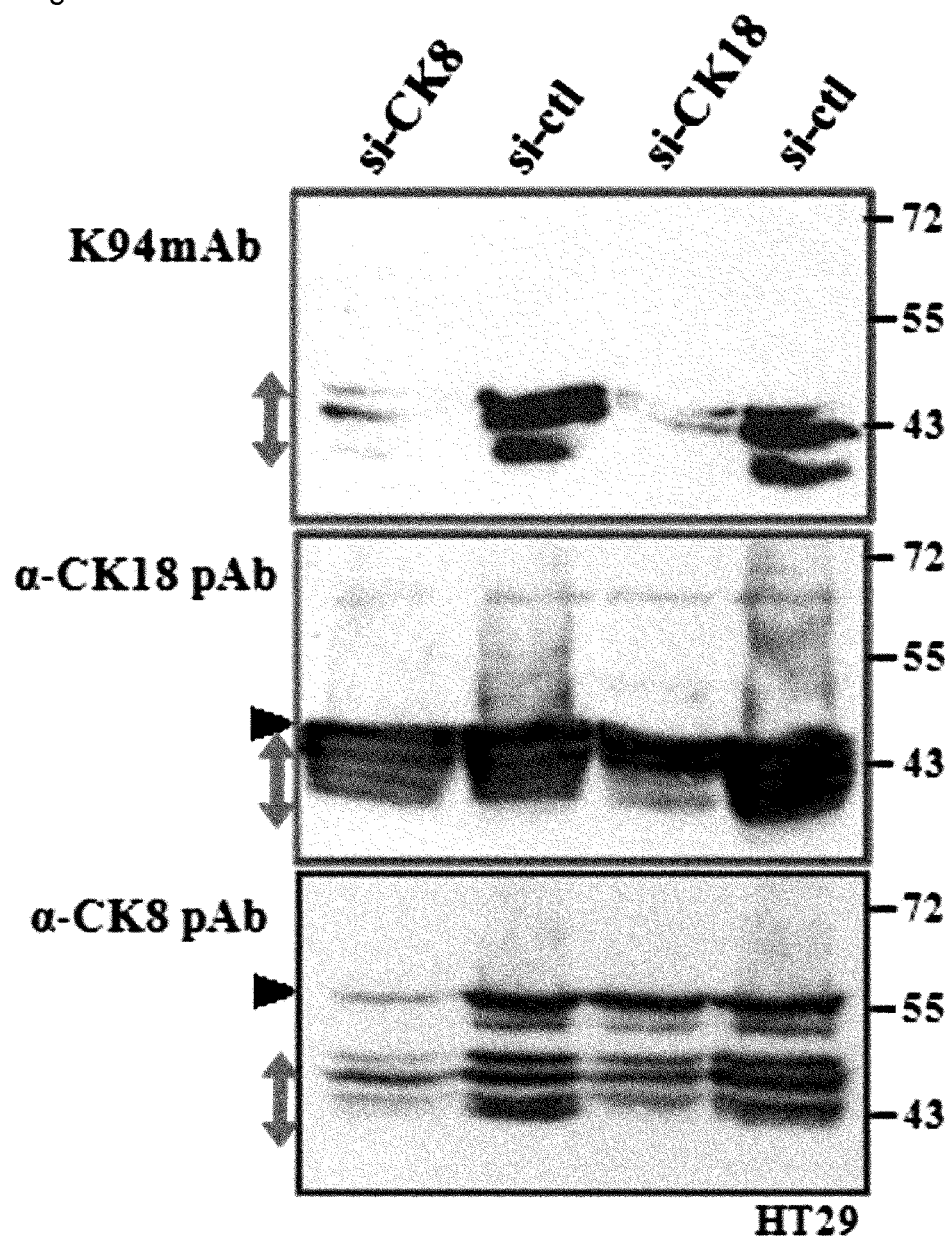
FIG. 6 shows a difference in TAB-K94 antibody reactivity after suppression of CK8 or CK18 expression by treatment of MCF-7 and HT29 cells with CK8 or CK18-specific siRNA in order to confirm CK8 and CK18 identified as TAB-K94 antibody-specific antigens. (A) is the result of RT-PCR to examine suppression of CK8 or CK18 expression. (B and C) show the results of flow cytometry and Western blotting analysis using the TAB-K94 antibody. When each expression of CK8 and CK18 was suppressed, K94 antibody reaction was reduced in both cases.
Figure 10:
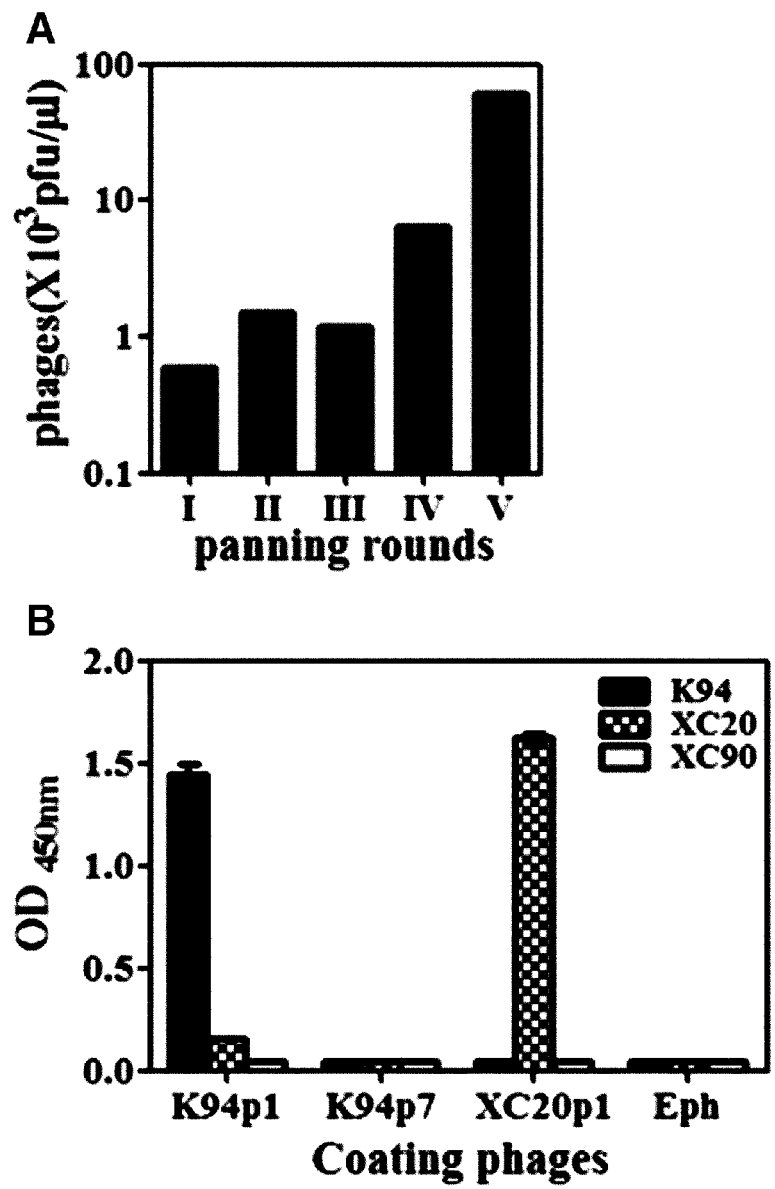
FIG. 10 shows the result of phage peptide library screening for TAB-K94 antibody. By the screening, phages expressing TAB-K94 antibody-specific antigen were selected. 5 rounds of panning were performed using TAB-K94 antibody. (A) shows the number of amplified phages according to the number of panning rounds, and two phages having different peptide sequences (K94p1, K94p7) were selected. (B) is the result of ELISA to examine the reactivity of the selected phages to TAB-K94 antibody, showing that the K94p1 phage has the TAB-K94 antibody-specific reactivity.

Furthermore, the present inventors examined a specific epitope sequence using a phage display-peptide library consisting of 7 amino acids, in order to identify the epitope sequence binding to the purified autoantibody (Table 2). ELISA was performed using the identified phage sequence as a coating antigen and the identified autoantibody as a primary antibody, so as to identify antigen groups showing high reactivity. An antigen showing the highest reactivity (identified by the phage libraries designated as K94p1 and K94p7) was found and designated as K94 antigen or K94-autoantigen (FIG. 10). In addition, the type and function of the identified antigen were examined. As a result, the corresponding antigen was found to be a cytokeratin 8/18 complex (FIGS. 5, 6, and 7, and Table 1).

In still another embodiment, the present invention provides a medium cell line producing the autoantibody of the present invention.

As used herein, the term "medium" refers to a cell resulting from the artificial fusion of two different cells, and a fused cell of two or more homogenous cells or heterogeneous cells prepared by using a substance inducing cell fusion such as polyethylene glycol or a type of virus. A hybridoma is to integrate different functions of different cells into one cell, and is represented by lymphocytes. In particular, a hybrid cell, which is prepared by the fusion of myeloma cells and B cell which is a precursor cell responsible for producing antibodies among lymphocytes in the spleen or lymph node, produces monoclonal antibodies, and is thus widely used in researches or clinical trials. In addition, hybridomas of lymphokines (physiologically active substance)-producing T cells and their tumor cells are also practically used. The hybridoma producing the autoantibody of the present invention may be suitably prepared by modification of the cells known in the art by those skilled in the art. In one Example of the present invention, a mouse myeloma cell Sp2/0 and B cell were fused and cultured, and then B cell hybridomas producing liver cancer cell-reactive antibodies only were selected, and designated as TAB-K94, which was deposited at Biological Resource Center, Korea Research Institute of Bioscience and Biotechnology under the Accession No. KCTC 11799BP on Oct. 29, 2010. Preferably, the hybridoma cell line may be a cell line of Accession No. KCTC 11799BP.

In still another embodiment, the present invention provides a kit for diagnosing breast cancer comprising the composition of the present invention.

As used herein, the term "antigen specifically binding to cytokeratin 8/18 complex-specific autoantibody" includes all proteins capable of specifically binding to the autoantibody, and is not limited to particular proteins or polypeptides. Preferably, the antigen may include any fragment thereof or any variant thereof, as long as it can be recognized by the cytokeratin 8/18 complex-specific autoantibody. The antigen may be composed of 7 to 16 amino acids, and preferably may include 430 or 483 amino acids. More preferably, the antigen may be an epitope sequence that can be recognized by the autoantibody marker of the present invention. The epitope sequence is not limited in its size or type, as long as it is a sequence recognized by the autoantibody of the present invention, and preferably the epitope sequence may be a polypeptide sequence consisting of 7 amino acids. The sequence consisting of 7 amino acids may be a sequence including one or more polypeptides selected from the group consisting of ISPDAHS (Ile-Ser-Pro-Asp-Ala-His-Ser), TLSHTRT (Thr-Leu-Ser-His-Thr-Arg-Thr), ISPGAHS (Ile-Ser-Pro-Gly-Ala-His-Ser), IAPDAHS (Ile-Ala-Pro-Asp-Ala-His-Ser), ISADAHS (Ile-Ser-Ala-Asp-Ala-His-Ser), ISPDAAS (Ile-Ser-Pro-Asp-Ala-Ala-Ser), and ISPDAHA (Ile-Ser-Pro-Asp-Ala-His-Ala), but the type of the sequence recognized by the autoantibody of the present invention is not limited to these examples. The present inventors identified the sequence that is recognized by the autoantibody of the present invention using 7 peptide display phages. As a result, the autoantibody of the present invention was found to show significantly high reactivity to the sequence of ISPDAHS (Ile-Ser-Pro-Asp-Ala-His-Ser) (Table 2).

The diagnostic kit for breast cancer of the present invention may include not only a primer to measure the expression level of the cytokeratin 8/18 complex as a diagnostic marker for breast cancer, a probe or an antibody selectively recognizing the marker but also one or more compositions of other components, a solution, or an apparatus, which are suitable for the analysis method.

Further, the kit for measuring the expression level of the protein expressed from the gene encoding the diagnostic marker cytokeratin 8/18 complex gene may include a matrix, a suitable buffer solution, a coloring enzyme, or a secondary antibody labeled with a fluorescent substance, a coloring substrate or the like for the immunological detection of the antibody. As for the matrix, a nitrocellulose membrane, a 96 well plate made of polyvinyl resin, a 96 well plate made of polystyrene resin, and a slide glass may be used. As for the coloring enzyme, peroxidase and alkaline phosphatase may be used. As for the fluorescent substance, FITC and RITC may be used, and as for the coloring substrate solution, ABTS (2,2'-azino-bis-(3-ethylbenzothiazoline-6-sulfonic acid)), OPD (o-phenylenediamine), or TMB (tetramethyl benzidine) may be used.

Analysis methods for measuring the protein level include, but are not limited to, Western blotting, ELISA (Enzyme Linked Immunosorbent Assay), radioimmunoassay (otA), radioimmunodiffusion, Ouchterlony immunodiffusion, rocket immunoelectrophoresis, immunohistostaining, immunoprecipitation assay, complement fixation assay, FACS, and protein chip assay, and preferably, the kit of the present invention may be a kit using ELISA coated with the cytokeratin 8/18 complex or an epitope of a cytokeratin 8/18 complex-specific autoantibody.

The protein expression level may be measured by ELISA. Examples of ELISA include direct ELISA using a labeled antibody recognizing an antigen immobilized on a solid support, indirect ELISA using a labeled antibody recognizing a capture antibody in antibody complexes recognizing an antigen immobilized on a solid support, direct sandwich ELISA using another labeled antibody recognizing an antigen in an antigen-antibody complex immobilized on a solid support, and indirect sandwich ELISA, in which another labeled antibody recognizing an antigen in an antigen-antibody complex immobilized on a solid support is reacted, and then a labeled secondary antibody recognizing the former antibody is used. For example, the protein expression levels are detected by sandwich ELISA, where a sample reacts with an antibody immobilized on a solid support, and the resulting antigen-antibody complexes are detected by adding a labeled antibody specific to the antigen, followed by enzymatic color development, or by adding a labeled secondary antibody specific to the antibody which recognizes the antigen of the antigen-antibody complex, followed by enzymatic development. The incidence of breast cancer may be diagnosed by measuring the degree of complex formation of the diagnostic marker, cytokeratin 8/18 complex and an antibody thereto. In one Example of the present invention, the epitope sequence reacting with the autoantibody of the present invention was identified using 7 peptide phage libraries, and reacted with a primary antibody, and then with IgGAM-HRP, followed by examination of the antigen-antibody complex formation and the amount thereof. As a result, there was a clear difference in the patterns between the sera of normal individuals and those of breast cancer individuals.

When detection of the cytokeratin 8/18 complex-specific autoantibody or diagnosis of breast cancer is performed in such a manner, breast cancer can be diagnosed with high specificity and sensitivity. In the preferred embodiment of the present invention, ELISA (Enzyme-linked immunosorbent assay) was used to perform the detection. As a result, individuals with breast cancer can be diagnosed and distinguished from normal individuals with 50% sensitivity and 82.61% specificity.

Further, Western blotting may be performed using one or more antibodies against the diagnostic marker. Total proteins are isolated from a sample, electrophoresed to be separated according to size, transferred onto a nitrocellulose membrane, and reacted with an antibody. The amount of proteins produced by gene expression is determined by measuring the amount of produced antigen-antibody complexes using a labeled antibody, thereby diagnosing the incidence of breast cancer.

In addition, the protein expression levels are measured by immunohistostaining using one or more antibodies against the marker. Tissue samples from breast cancer patients or individuals suspected of having breast cancer were collected and fixed, and then paraffin-embedded blocks were prepared according to a widely known method. The blocks were cut into small sections several μm in thickness, and attached to glass slides to be reacted with the fragment including the antigen-binding site of the autoantibody of the present invention according to a known method. Subsequently, the unreacted antibodies were washed, and the reacted antibodies were labeled with one selected from the above mentioned detection labels, and then observed under a microscope.

A protein chip, in which one or more antibodies against the marker are arranged and fixed at a high density at predetermined positions on a substrate, may be used. In this regard, proteins are separated from a sample and hybridized with a protein chip to form an antigen-antibody complex, which is then read to examine the presence or expression level of the protein of interest, thereby diagnosing the occurrence of breast cancer.

In still another embodiment, the present invention provides a method for diagnosing breast cancer, comprising the step of detecting an cytokeratin 8/18 complex-specific autoantibody or a fragment comprising the antigen-binding site thereof using the composition of the present invention.

Preferably, the method for detecting the cytokeratin 8/18 complex-specific autoantibody of the present invention may include the steps of (a) measuring an expression level of the cytokeratin 8/18 complex-specific autoantibody or the fragment including the antigen-binding site thereof in a biological sample from a patient with suspected breast cancer; and (b) comparing the measured protein level with that of a normal control sample.

As used herein, the term "individual" includes horses, dogs, cats, pigs, goats, rabbits, hamsters, monkeys, guinea pigs, rats, mice, lizards, snakes, sheep, cattle, fish, and birds without limitation, and may mean any animal (e.g., human), and widely includes cell lines of the animals without limitation.

As used herein, the term "control group" is a sample derived from an individual showing lower expression level of cytokeratin 8/18 complex-specific autoantibody than breast cancer or suspected breast cancer, and refers to a sample to be used as a standard for the diagnosis of breast cancer by antigen-antibody reaction using the cytokeratin 8/18 complex-specific autoantibody of the present invention.

As used herein, the term "sample" refers to any one or more samples selected from the group consisting of whole blood, serum, blood, plasma, saliva, urine, sputum, lymphatic fluid, cerebrospinal fluid, and interstitial fluid that shows a difference in the expression levels of the diagnostic marker for breast cancer, cytokeratin 8/18 complex-specific autoantibody, but is not limited thereto.

Further, analysis methods for measuring the protein expression level include Western blotting, ELISA (Enzyme Linked Immunosorbent Assay), radioimmunoassay (otA), radioimmunodiffusion, Ouchterlony immunodiffusion, rocket immunoelectrophoresis, immunohistochemical staining, immunoprecipitation assay, complement fixation assay, FACS, and protein chip assay, but the methods for measuring the protein expression level are not limited to these examples.

In still another embodiment, the present invention provides a method for screening a therapeutic agent for breast cancer, comprising the steps of (a) measuring an expression level of an cytokeratin 8/18 complex-specific autoantibody; (b) administering a candidate therapeutic agent for breast cancer; and (c) examining whether the expression level of the cytokeratin 8/18 complex-specific autoantibody is reduced, compared to that in step (a).

In step (a), the step of measuring the expression level of the cytokeratin 8/18 complex-specific autoantibody may be performed by the methods commonly used in the art without limitation, and examples thereof include Western blotting, ELISA (Enzyme Linked Immunosorbent Assay), radioimmunoassay (otA), radioimmunodiffusion, Ouchterlony immunodiffusion, rocket immunoelectrophoresis, immunohistostaining, immunoprecipitation assay, complement fixation assay, FACS, and protein chip assay.

Steps (b) and (c) are the steps of screening a therapeutic agent for breast cancer, including the steps of administering a candidate therapeutic agent for breast cancer and examining whether the expression level of the cytokeratin 8/18 complex-specific autoantibody is reduced, compared to that before treatment of the candidate material.

As used herein, the term "candidate therapeutic agent for breast cancer" refers to a substance expected to treat breast cancer. Any substance can be used without limitation, as long as it is expected to directly or indirectly ameliorate or improve breast cancer. It includes all candidate therapeutic substances such as compounds, genes or proteins. The screening method of the present invention examines the expression levels of cytokeratin 8/18 complex-specific before and after administration of the candidate substance. When the expression level is decreased, compared to that before administration, the corresponding candidate substance can be determined as a therapeutic agent for breast cancer.

In still another embodiment, the present invention provides the use of a cytokeratin 8/18 complex-specific autoantibody or a fragment comprising an antigen-binding site thereof in the diagnosis of breast cancer.

Hereinafter, the present invention will be described in more detail with reference to the following Examples. However, these Examples are for illustrative purposes only, and the invention is not intended to be limited thereby.

Example 1

Acquisition of a Group of Autoantibody-Producing Cells and K94 Autoantibody-Producing Cell In order to acquire autoantibodies produced during carcinogenesis, an H-ras12V transgenic mouse that was reported to develop liver cancer similar to human liver cancer was utilized. Spleen cells were obtained from H-ras12V transgenic mice with liver cancer as a B cell group, and fused with a mouse myeloma cell Sp2/0 to prepare a B cell hybridoma cell line. The cell fusion was performed according to the common B cell hybridoma preparation method. Primary selection of the fused cells was performed using HAT medium (hypoxanthine-aminopterin-thymidine medium), and only clone-forming cells were cultured separately. Among those cultured cells, the cells, in whose culture medium, cancer cell-reactive antibodies were detected were only selected and maintained.

The reactivity of autoantibodies against cancer cells was examined by flow cytometric analysis of cancer cell line after intracellular staining following the fixation and permeabilization. The method is described in detail as follows. A liver cancer cell line, HepG2 or Hepa1c1c7 at 70-80% confluency was treated with trypsin, detached from the cell culture plate, and washed with PBS. 100 µl of Cytofix/Cytoperm solution (BD) per $2 \times 10^5$ cells was added thereto, and the cells were incubated at 4° C. for 20 minutes for fixation and permeabilization. After incubation, 1 ml of Cytowash/Cytoperm solution (BD) was added and mixed well. Then the mixture was centrifuged at 1700 rpm for 5 minutes and the cell pellet was washed. 50 µl of a primary antibody solution (B cell hybridoma cell culture medium or purified primary antibody solution) was added to the washed sample, and the incubation was performed at 4° C. for 40 minutes. After incubation, the cells were washed three times, and treated with anti-mouse Igs-RPE (DaKo) at 4° C. for 40 minutes. Then, the cells were washed an additional three times, and the cell pellet was resuspended in 300 µl of PBS, followed by analysis using a FACSCaliber (BD). Mean values of fluorescence corresponding to antibody reactions were obtained and compared. 50 µl of mouse antibody free DMEM medium was added to the control group showing no antibody reaction.

As a result, many autoantibody-producing clones were obtained. Among them, a TAB-K94 monoclonal antibody was investigated in the present invention (FIG. 1).

A hybridoma cell line producing the TAB-K94 monoclonal antibody was deposited at the Biological Resource Center (KCTC), Korea Research institute of Bioscience and Biotechnology (KRIBB) under the Accession No. KCTC 11799BP on Oct. 29, 2010.

Example 2

Purification of TAB-K94 Monoclonal Antibody

For the analysis of antigens against TAB-K94 autoantibodies, purified antibodies were required. Cell culture medium obtained by culturing a large amount of TAB-K94 antibody-producing clones or TAB-K94 antibody-producing cells were injected into the peritoneal cavity of mice, thereby acquiring ascites fluid and using it for antibody purification. The generally used isotyping ELISA was used to identify that the type of TAB-K94 antibody was IgM. MBP-agarose (Mannose binding protein immobilized agarose: Pierce) or protein L agarose was used in affinity chromatography for IgM purification. After SDS-electrophoresis, the purified antibodies were examined by coomassie staining, and protein quantification was performed before use (FIG. 2).

Example 3

Reactivity of TAB-K94 Antibody Against Cancer Cell Lines and Immunohistochemical Staining of Breast Cancer Tissue The reactivity of TAB-K94 autoantibodies against various cancer cell lines was examined by flow cytometric analysis after intracellular staining of various cancer cell lines in the same manner as in Example 1 (FIG. 3A). As a result, expression of TAB-K94 antibody-reactive proteins was noticeably increased in a liver cancer cell line, HepG2 and a breast cancer cell line, MCF-7 (FIG. 3A).

Based on the reactivity against cancer cells, expression of TAB-K94 antibody-reactive antigen was examined by immunohistostaining of human liver cancer tissues and breast cancer tissues using TAB-K94 antibodies. As a result, no distinct reaction was observed in the liver cancer tissues (data not shown), but a strong staining around cell membrane was observed in the breast cancer tissues, in particular, in the invasive front (FIG. 3B). These results suggest that the TAB-K94 antigen is more useful for the diagnosis of breast cancer than liver cancer.

Example 4

Analysis of Complementarity Determining Region (CDR) of TAB-K94 Antibody

It was confirmed that TAB-K94 antibodies specifically recognize antigens overexpressed in cancer cells. In order to obtain information about antigen specificity of the TAB-K94 antibody, sequencing of complementarity determining region (CDR) of the corresponding antigen was performed. The detailed method is as follows:

About $10^6$ cells of TAB-K94 antibody-producing cells were collected and total RNA was extracted therefrom using an RNA extraction kit (Qiagen). cDNA was synthesized from 5 μg of total RNA using a complementary DNA (cDNA) synthesis kit (Invitrogen). CDR containing regions of mouse heavy chain and light chain were amplified by polymerase chain reaction (PCR) using 1 μg of the synthesized cDNA and mouse heavy chain primers of 5'-CTT CCG GAA TTC SAR GTN MAG CTG SAG SAG TCW GG-3' (SEQ ID NO. 17) and 5'-GGA AGA TCT GAC ATT TGG GAA GGA CTG ACT CTC-3' (SEQ ID NO. 18) and mouse light chain primers of 5'-GGG AGC TCG AYAT TGT GMT SAC MCA RWC TMC A-3' (SEQ ID NO. 19) and 5'-GGT GCA TGC GGA TAC AGT TGG TGC AGC ATC-3' (SEQ ID NO. 20). As a PCR reaction mixture, 10× buffer diluted to a final concentration of 1×, 2 μl of cDNA, 10 mM of dNTP (2.5 mM/μl), 5 U of nPfu polymerase (Enzynomix, 5 U/μl), and 2 pmole of each primer were mixed, filled up with water to a final volume of 50 μl, and melted at 94° C. for 3 minutes. Amplification was performed for 30 cycles of 94° C. for 1 minute, 63° C. for 1 minute, and 72° C. for 2 minutes, elongation was performed at 72° C. for 10 minutes, and then the product was cooled to 4° C. After amplification, the product was ligated into a pTOP Blunt V2 vector using a TOPcloner Blunt kit (Enzynomics). The recombinant plasmid was transformed into E. coli. DH5α, spread onto LB defined media plates supplemented with ampicillin, and cultured at 37° C. for 15 hours. One of the colonies formed on the plate was cultured in LB liquid defined medium for 12 hours or longer, and plasmids were extracted, followed by sequencing analysis. From the analyzed base sequence, the protein sequence was determined, and analyzed according to the Kabat CDR definition so as to determine the CDR of the TAB-K94 antibody.

As a result, the TAB-K94 autoantibody was found to have the heavy chain CDR1 represented by SEQ ID NO. 11, CDR2 represented by SEQ ID NO. 12, and CDR3 represented by SEQ ID NO. 13, and the light chain CDR1 represented by SEQ ID NO. 14, CDR2 represented by SEQ ID NO. 15, and CDR3 represented by SEQ ID NO. 16 (FIG. 4).

Example 5

Expression of TAB-K94 Antibody-Specific Antigens in Various Cancer Cells and Identification of Antigen Protein Expression of TAB-K94 antibody-specific antigen proteins was examined in various cancer cell lines by Western blotting (FIG. 5A). The detailed method is as follows. The cells to be analyzed were collected and dissolved in PBS containing RIPA buffer (0.1% (w/v) SDS, 0.1% (w/v) sodium deoxycholate, 1.0% (v/v) NP40, protease inhibitor cocktail (Roche)) to be used as protein analysis samples. Protein quantification was performed by Bradford assay. Each 50 μg of the prepared protein samples was run on 10% reduced SDS-PAGE, and transferred onto a PVDF membrane. Thereafter, the membrane was blocked in a 5% (w/v) skim milk/TBS (Tris-buffered saline), and treated with a primary antibody. Purified TAB-K94 antibodies were diluted in the blocking solution at a concentration of 10 μg/ml, and then used as the primary antibody. After treatment of the primary antibody, the antibodies were thoroughly washed with TBST (TBS containing 0.02% (v/v) tween-20), and treated with a secondary antibody (anti-mouse IgGAM-HRP). Subsequently, the antibody-reactive protein bands were detected by ECL (enhanced chemiluminescence). As a result, the TAB-K94 antibody-specific antigens were found in the liver cancer cell lines including Hep3B, PLC/PRF/5, and SK-Hep1 as a band having a molecular weight of 45 kDa. Interestingly, overexpression of the TAB-K94 antibody-reactive protein was observed in the colon cancer cell, HT29 and the breast cancer cell, MCF-7 (FIG. 5A).

For induction of antibodies in the individual, a specific protein should be released into the blood. That is, extracellular release of proteins expressed within the cells supports the induction of autoantibodies. Therefore, the presence of antigens was examined in the cell culture medium of cell lines expressing TAB-K94 antibody-specific antigens by Western blotting. Each 10 ml of serum-free cell culture medium was collected, and concentrated, and each 50 μg of the quantified protein was run on 10% reduced SDS-PAGE. Western blotting was performed in the same manner as above. As a result, excessive release of TAB-K94 antibody-specific antigens was observed in the breast cancer cell line, MCF-7 (FIG. 5A).

In order to identify TAB-K94 antibody-specific antigen proteins, the TAB-K94 antibody-specific antigen proteins partially purified from serum-free MCF-7 culture medium were analyzed by mass spectrometry. The detailed method is as follows: 500 ml of serum-free MCF-7 culture medium was collected, and concentrated to obtain 6 mg of the protein, followed by fractionation using a HiTrap-Q (GE healthcare) column. From the results of Western blotting of each fraction, a fraction including the TAB-K94 antibody-specific antigen proteins was selected, and precipitated with acetone for concentration. The concentrated antigen protein solution was separated on 8 to 10% SDS-PAGE, and a part thereof was used for Western blotting to examine the presence of TAB-K94 antigens, and the rest was used for coomassie staining to examine the protein bands. The protein bands corresponding to the TAB-K94 antibody reaction were cut out, and subjected to in-gel digestion using the protease trypsin (FIG. 5B). After in-gel digestion, the extracted peptide fraction was subjected to mass spectrometry to obtain information regarding the protein sequence. As a result, the TAB-K94 antibody-specific antigens were found to be cytokeratin 8 (CK8) and cytokeratin 18 (CK18) (Table 1).

TABLE 1

Identification of specific antigen against TAB-K94 antibody

| position | protein | Accession number | Molecular mass (Da) | Queries matched | Mascot score |
|---|---|---|---|---|---|
| 1 | KRT18 Keratin, type I cytoskeletal 18 | IP00554788 | 48029 | 69 | 1298 |
|   | KRT8 Keratin, type II cytoskeletal 8 | IP00554648 | 53671 | 56 | 931 |
| 2 | KRT18 Keratin, type I cytoskeletal 18 | IP00554788 | 48029 | 100 | 2310 |
|   | KRT8 Keratin, type II cytaskeletal 8 | IP00554648 | 53671 | 67 | 1120 |

Example 6

Identification of TAB-K94 Antibody-Specific Antigen Protein

In order to confirm the result of the protein identification by mass spectroscopy, a reduction in TAB-K94 antibody reaction was examined in the cells of which the expression of CK8 and CK18 was suppressed by using siRNAs. The detailed method is as follows:

As siRNAs for the suppression of CK8 and CK18 expression, siRNAs (CK8 Sense: 5'-CCG CAG UUA CGG UCA ACC A(dTdT)-3' (SEQ ID NO. 23), Antisense: 5'-UGG UUG ACC GUA ACU GCG G(dTdT)-3' (SEQ ID NO. 24), CK18 Sense: 5'-CUC ACA GAG CUG AGA CGU A(dTdT)-3' (SEQ ID NO. 25), Antisense: 5'-UAC GUC UCA GCU CUG UGA C(dTdT)-3' (SEQ ID NO. 26)) provided by Bioneer were used, and injected into MCF-7 or HT29 cells using Lipofectamine 2000 (Invitrogen). 72 hours after siRNA treatment, the cells were collected to extract total RNA, and 5 µg of RNA was used as a template to synthesize cDNA. The synthesized cDNA was used as a template to perform polymerase chain reaction using primers having specificity to CK8 and CK18. The resulting product was analyzed on a 1% agarose gel. As a result, the expression of CK8 and CK18 was found to be suppressed to by 50% or more (FIG. 6A).

The cells showing the suppressed CK8 and CK18 expression by siRNA in RT-PCR were subjected to flow cytometry in the same manner as in Examples 1 and 3, in order to examine their TAB-K94 antibody reaction. As a result, reduced TAB-K94 antibody reaction was observed in the cells having the suppressed CK8 or CK18 expression (FIG. 6B), suggesting that each expression of CK8 and CK18 is involved in the expression of TAB-K94 antibody-specific antigen. However, the previous studies reported that CK and CK18 form a complex to exert intracellular function. Therefore, it can be assumed that variation in the expression of one of the two proteins affects that of the other protein, and this assumption was examined by Western blotting. After treatment of siRNA for CK8 or CK18, Western blotting was performed using specific antibody to each. As a result, the suppression of each protein remarkably decreased the amount of the TAB-K94 antibody-specific antigens. According to the result of detection using CK8-specific or CK18-specific antibody, the amount of each protein was found to be reduced by half. In particular, the protein bands corresponding to the truncated forms of the two proteins were also greatly reduced in intensity (FIG. 6C), suggesting that TAB-K94 antibody reaction is detected upon complex formation of CK8 and CK18 proteins.

Example 7

Identification of TAB-K94 Antibody Binding Site: Reactivity to CK8/18 Complex

In Example 6, it was confirmed that the TAB-K94 antibody-specific antigen protein is a CK8/CK18 complex. For further confirmation, CK8 and CK18 recombinant proteins were prepared to examine the reactivity of TAB-K94 antibody against each protein and a mixture thereof. The detailed method is as follows:

For cloning of human CK8 and CK18 genes, PCR was performed using each of the specific primers (CK8 F: 5'-CCG CAT ATG ATG TCC ATC AGG GTG ACC-3' (SEQ ID NO. 32), R: 5'-ATA GTC GAC CTT GGG CAG GAC GTC AGA-3' (SEQ ID NO. 33), CK18 F: 5'-CCG GAA TTC ATG AGC TTC ACC ACT CGC-3' (SEQ ID NO. 34), R: 5'-ATA CTC GAG ATG CCT CAG AAC TTT GGT-3' (SEQ ID NO. 35)), nPfu DNA polymerase (Enzynomix) and 100 ng of MCF-7 cell-derived cDNA as a template. The obtained gene and a pET29a(+) vector (Novagen) were treated with restriction enzymes (CK8: NdeI/SalI, CK18: EcoRI/XhoI) at 37° C. for 15 hours, and the digested gene and vector were mixed at a predetermined ratio. Ligase (Roche) was added, and ligation was performed at 16° C. for 16 hours. The ligation mixture was transformed into DH5α, spread on an LB defined media plate supplemented with kanamycin, and cultured at 37° C. for 15 hours. Colonies formed on the plate were selected and cultured in LB defined liquid media to isolate the amplified recombinant plasmids. A base sequence of the isolated plasmid was analyzed and transformed into the BL21 (DE3) strain again, so as to express CK8 and CK18 recombinant proteins. The protein expression was induced by addition of IPTG, and the cells were cultured at 37° C. for 4 hours after addition of IPTG to obtain the proteins. Each recombinant protein was obtained in a form of inclusion body, which was dissolved in an 8 M urea/PBS (pH 7.4) solution, and used for further experiments. The obtained recombinant proteins were run on a 10% SDS-PAGE singly or in a mixture, and bands corresponding to the expected molecular weights were detected by coomassie staining. The same gel was subjected to Western blotting, and a commercially available CK8-specific or CK18-specific antibody was used to examine whether the correct recombinant proteins were obtained (FIG. 7A). The reaction of TAB-K94 antibody against these proteins or mixture thereof was examined. As a result, each of CK8 and CK18 proteins showed no reactivity against the TAB-K94 antibody, whereas the mixture thereof showed reactivity against the TAB-K94 antibody.

The CK8/18 complex formation could be induced by Western blotting, and the reactivity of TAB-K94 antibody against the formed CK8/18 complex could be also observed. First, the CK8 or CK18 protein was run on SDS-PAGE, which was blotted onto PVDF membrane. The membrane was treated with 5% (w/v) skim milk/TBS (Tris-buffered saline), and then with CK8 or CK18 recombinant protein solution (50 µg/ml of recombinant protein dissolved in 0.1 M sodium bicarbonate, pH 8.6) at room temperature for 1 hour. The recombinant protein-treated membrane was washed with TBST (0.02% (v/v) tween-20-containing TBS), and treated with TAB-K94 antibody diluted in the blocking solution at a concentration of 10 µg/ml, at room temperature for 1 hour. The membrane was sufficiently washed with TBST, and treated with a secondary antibody (anti-mouse IgGAM-HRP). Then, the antibody-reactive protein bands were detected by ECL (enhanced chemiluminescence). As a result, the CK8 protein alone did not show reactivity against the TAB-K94 antibody, but the CK8/CK18 complex induced the reaction with the antibody (FIG. 7B). Moreover, the reactivity of CK8, CK18, and CK8/18 complex against TAB-K94 antibody was also examined by ELISA (Enzyme-Linked ImmunoSorbent Assay) (FIG. 7C). ELISA showed the same results as in the Western blotting. That is, reactivity of TAB-K94 antibody against each protein was not observed, but the reactivity was observed when the mixture of the two proteins was used as a coating antigen, indicating that the TAB-K94 antibody shows reactivity against the CK8/18 complex. It means that the TAB-K94 autoantibody of the present invention specifically binds to the CK8/18 complex.

Example 8

Fine Epitope Mapping of TAB-K94 Antibody Against CK8/18 Complex

Figure 8:
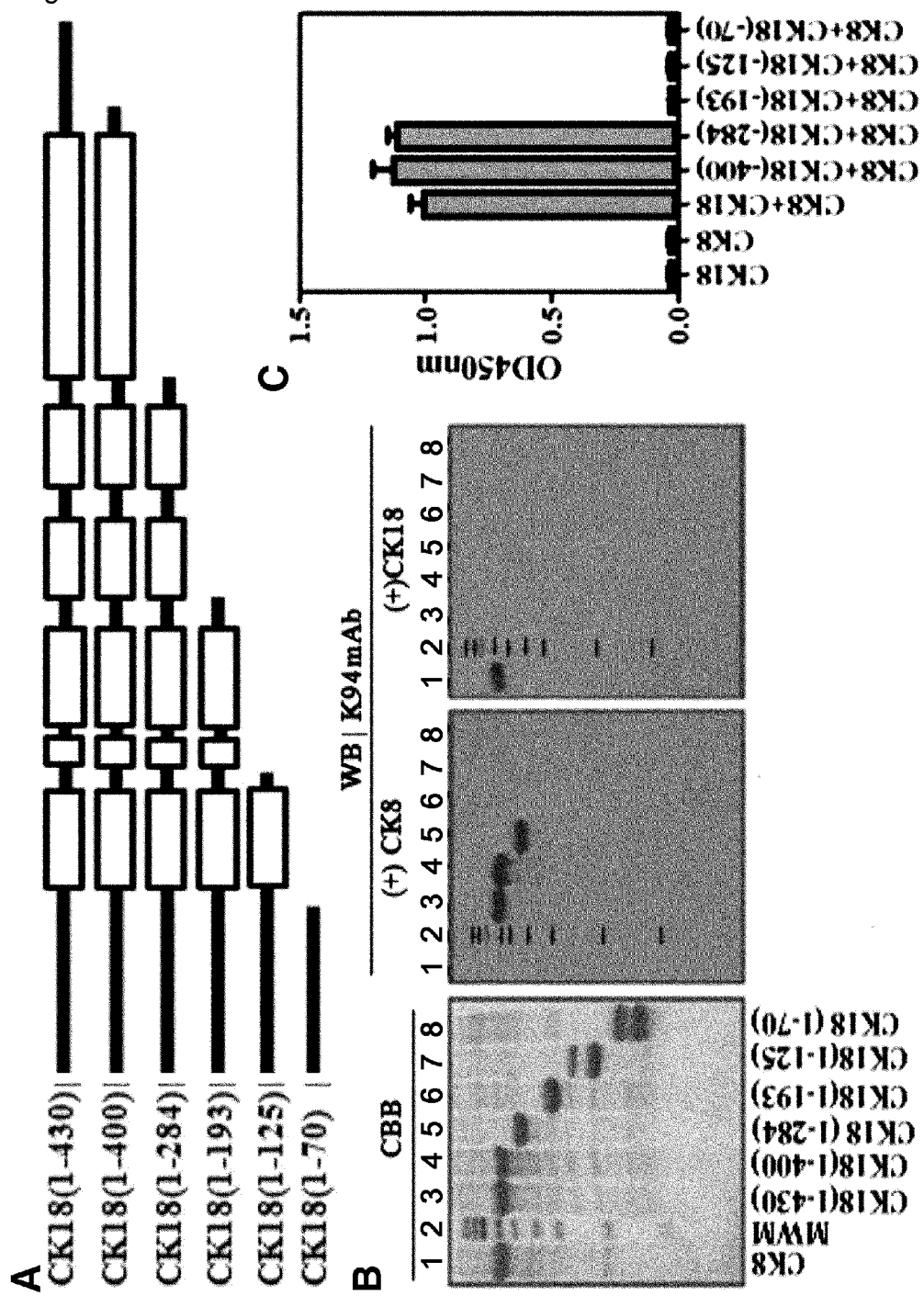
FIG. 8 shows the result of fine epitope mapping of TAB-K94 antibody. CK18 protein was prepared into truncated recombinant proteins varying in size. As schematically shown in (A), CK18 (amino acids 1-70), CK18 (amino acids 1-125), CK18 (amino acids 1-1.93), CK18 (amino acids 1-284), and CK18 (amino acids 1-400) were expressed as the CK18 truncated variants. Each recombinant protein was separated on SDS-PAGE and Western blotting was performed to examine the reactivity to TAB-K94 antibody after treatment of CK8 or CK18 recombinant protein, which is shown in (B). As a result, it was determined that a complex formed in the presence of a region corresponding to amino acids 194-284 of the CK18 only showed reactivity to TAB-K94 antibody. (C) is the result of ELISA to confirm the above result. Mixtures prepared by mixing CK8 recombinant protein and CK18 truncated recombinant proteins in an equal amount were coated thereto, and the reactivity to TAB-K94 antibody was examined.

For epitope mapping of TAB-K94 antibody against CK8/18 complex, various CK18 truncated recombinant proteins were prepared, and the reactivity of TAB-K94 antibody against CK8/CK18 complex formed thereby was analyzed. The detailed method is as follows. As the CK18 truncated forms, an expressed form of amino acids 1-70 of CK18 protein, an expressed form of amino acids 1-125 of CK18 protein, an expressed form of amino acids 1-193 of CK13 protein, an expressed form of amino acids 1-284 of CK18 protein, and an expressed form of amino acids 1-400 of CK18 protein were prepared in accordance with the above preparation method of the CK18 recombinant protein (FIG. 8A). The CK18 truncated recombinant proteins were separated on a 15% SDS-PAGE gel together with CK8 and CK18 recombinant proteins, followed by coomassie staining. The same gel was transferred onto a PVDF membrane, and then the membrane was treated with 50 µg/ml of CK8 or CK18 recombinant protein for 1 hour to induce complex formation. Thereafter, Western blotting was performed using TAB-K94 antibody, and the epitope of TAB-K94 antibody against CK8/18 complex was identified (FIG. 8B). In addition, the CK18 truncated recombinant proteins were treated with the CK8 recombinant protein to induce complex formation, and then the complex was used as a coating antigen to examine its reactivity to TAB-K94 antibody by ELISA (FIG. 8C).

Taken together, it was determined that amino acids 193-284 of the CK18 protein forms an epitope specific to the TAB-K94 antibody.

Example 9

Intracellular Localization of TAB-K94 Antigen Expression

Figure 9:
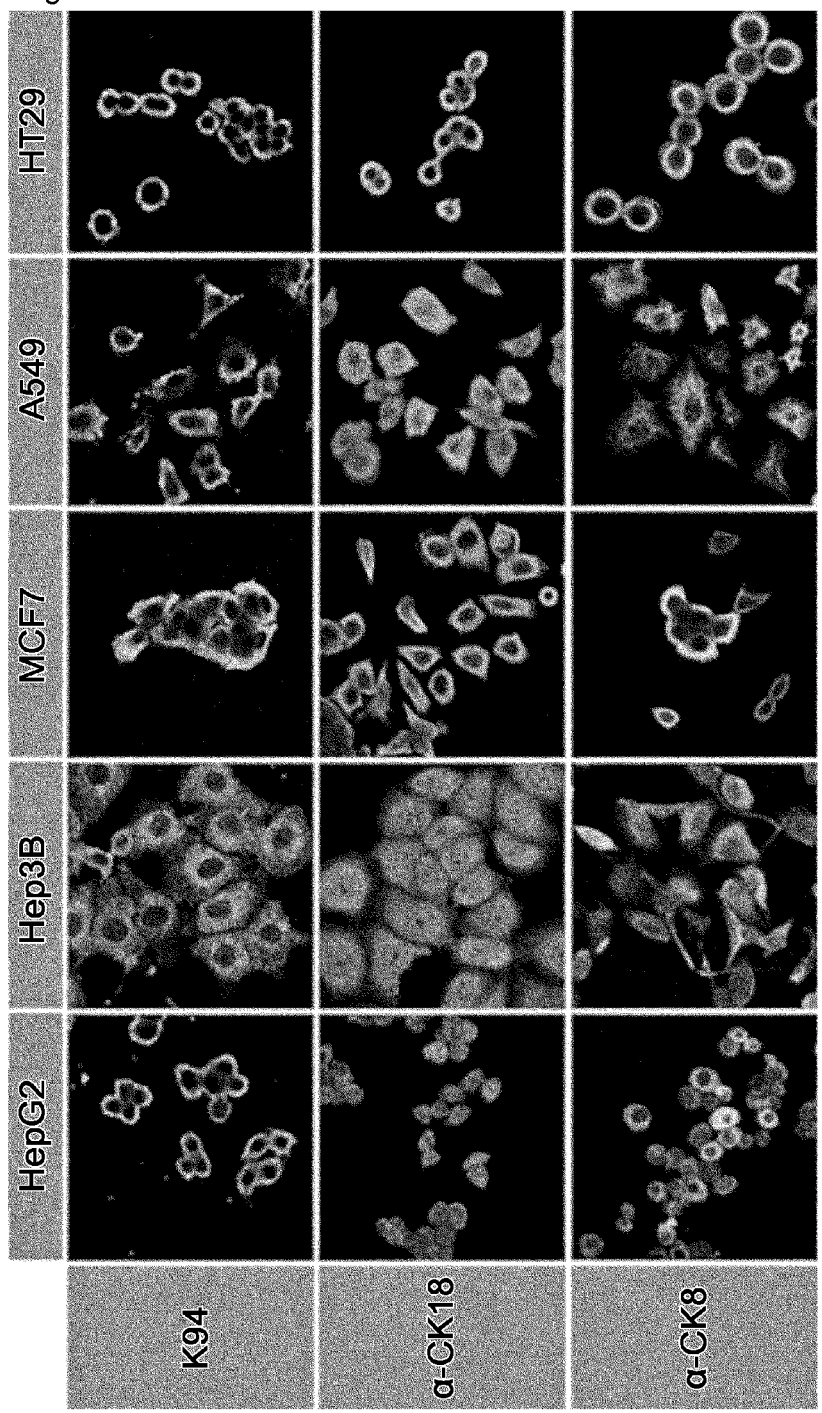
FIG. 9 shows the result of fluorescence staining for intracellular localization of TAB-K94 antibody and antigens recognized by CK8 or CK18 antibody. In the staining result of CK8 and CK18 proteins, the expression was observed throughout the cytoplasm and also in the nucleus, whereas in that of TAB-K94 antibody, staining was strongly localized in the cell membrane, corresponding to the region of CK8/18 complex formation.

In order to examine intracellular localization of the TAB-K94 antigen expression, the corresponding cells were cultured on a coverslip, and then intracellular staining was performed, followed by observation using confocal laser microscopy (Zeiss). As a primary antibody, the purified TAB-K94 antibody and CK8-specific or CK18-specific antibody were used at a concentration of 5 µg/ml, and as a secondary antibody, anti-mouse IgGAM-FITC was used. The stained coverslip was treated with a mounting solution containing DAPI, and placed on a slide. As shown in FIG. 9, TAB-K94 antibody-specific antigens were prominently observed in HepG2, MCF-7 and HT29 cells, and expressed throughout the entire cytoplasm, but strongly localized in the cell membrane. It was confirmed that the TAB-K94 antibody-specific antigen is a CK8/18 complex, and thus the cells were stained with CK8 and CK18-specific antibodies to compare with the localization of TAB-K94 antibody reaction. The TAB-K94 antibody reaction was observed in the overlapping regions of the expression of both antigens.

Example 10

Exploration of Phage Expressing TAB-K94 Antibody-Specific Peptide Antigen

The TAB-K94 antibody-specific epitope is the most important factor in the constitution of a method for detecting the presence of autoantibody against the same antigen site in the human serum. In order to use a reactive site with ease rather than the entire antigen protein as the TAB-K94 antibody-specific epitope, TAB-K94 antibody-specific peptide antigens were screened from the peptide expression library. Phase expressing cyclic peptide library (Ph.D.-C7C Phage Display Peptide Library kit; New England Biolabs) in which there are 7 amino acids randomly expressed and two additional cysteine residues at both termini to form a cyclic structure was used as the peptide expression library. The panning was performed in accordance with the manufacturer's instructions. The detailed method is as follows:

300 ng of TAB-K94 antibody and phage virions expressing $2 \times 10^{11}$ different peptides were mixed with each other in 200 µl of TBST solution, and reacted at room temperature for 20 minutes. The mixture was reacted with 25 µl of protein L-agarose bead pre-treated with a blocking solution (0.1 M $NaHCO_3$, pH 8.6, 5 mg/ml BSA, 0.02% (w/v) NaN3) at room temperature for 15 minutes. The antibody-reactive phages were subjected to centrifugation, and a cell pellet was recovered in a form of antibody-virion-protein L agarose conjugate. The cell pellet was washed with TBST several times, and eluted using 1 ml of elution buffer (pH 2.2) (0.2 M Glycine-HCl, pH 2.2, 1 mg/ml BSA). Immediately, 1 M Tris-HCl solution (pH 9.1) was added thereto for pH neutralization. A part of the eluted phages was used for titration, and the rest was used for phage amplification. The amplified phages were subjected to panning in the same manner as above.

As a result, five rounds of panning were performed using TAB-K94 antibody, and phages having two different peptide sequences were obtained. During the panning using TAB-K94 antibody, the number of the amplified phage was increased 10-fold at each round after the third round of panning, indicating an increase in the number of specific binding phages (FIG. 10A). 10 phages were randomly selected from the phages obtained from the last round of panning, the sequences of the peptides were determined by DNA sequencing analysis, and the amino acid sequences obtained therefrom were summarized in the Table below (Table 2).

TABLE 2

Insert peptide sequences of peptide-display phage selected by TAB-K94 antibody

| Phage | Epitope sequences | Frequency |
|---|---|---|
| K94-p1 | Ile Ser Pro Asp Ala His Ser | 9/10 |
| K94-p2 | Ile Ser Pro Asp Ala His Ser | |
| K94-p3 | Ile Ser Pro Asp Ala His Ser | |
| K94-p4 | Ile Ser Pro Asp Ala His Ser | |
| K94-p5 | Ile Ser Pro Asp Ala His Ser | |
| K94-p6 | Ile Ser Pro Asp Ala His Ser | |
| K94-p7 | Thr Leu Ser His Thr Arg Thr | 1/10 |
| K94-p8 | Ile Ser Pro Asp Ala His Ser | |
| K94-p9 | Ile Ser Pro Asp Ala His Ser | |
| K94-p10 | Ile Ser Pro Asp Ala His Ser | |

Example 11

ELISA for Detection of Phage Expressing Antibody-Specific Peptide

In order to examine the reactivity of the selected TAB-K94 antibody-specific phages against TAB-K94 antibody, ELISA was performed using the phage as a coating antigen and TAB-K94 antibody as a primary antibody. The detailed method is as follows:

The result of peptide sequencing analysis showed that two phages (K94p1, K94p7) having different sequences were selected, and the phages were amplified and partially purified using a PEG/NaCl solution, and then used as an ELISA coating antigen. 10 of the purified phage was diluted in 100 µl of a coating solution (0.1 M sodium bicarbonate buffer, pH 8.6) and added to each well of 96-well Maxisorp ELISA plate. For antigen coating, the phage-added plate was stored at 4° C. for 16 hours or longer. After phage coating, 300 µl of skim milk solution (5% (w/v) skim milk/TBST) was added, and reacted at room temperature for 1 hour to block the remaining sites after antigen coating. After blocking, the plate was washed with TBST (TBS containing 0.1% Tween-20) twice, and 100 ng/100 µl of TAB-K94 antibody was added thereto, and reacted at room temperature for 90 minutes. Thereafter, the plate was washed with TBST six times, and treated with a secondary antibody, anti-mouse IgGAM-HRP (Pierce) diluted at a ratio of 1:2500. The secondary antibody was also reacted at room temperature for 90 minutes, and the plate was washed with TBST six times. Color development was performed using a TMB solution (Pierce) as a substrate for HRP. Absorbance was measured at 450 nm to quantify the antigen-antibody reaction.

Of the two phages used as an antigen, K94p1 showed high reactivity against TAB-K94 antibody, but K94p7 showed no reactivity (FIG. 10 and Table 2). Thus, an epitope represented by SEQ ID NO. 21 was finally selected.

Example 12

Determination of Presence of TAB-K94 Like Autoantibody in Patient Serum Using K94p1 Antibody-Reactive Site-Expressing Phage In general, an epitope of an antigen which induces antibody reaction by stimulation of the immune system has a length of 20 amino acids or less corresponding to a specific part of the entire protein structure. In addition, the epitope is known to exert similar functions even on different individuals such as human, mouse, and goat. Based on this fact, the autoantibody-reactive epitope obtained from liver cancer model mouse is expected to show similar functions in the human body. Therefore, it was examined whether the K94p1 phage showing TAB-K94 antibody-specific reactivity is able to detect the autoantibody in the human serum when applied in the detection of human autoantibody. The detailed method is as follows:

$10^{10}$ of K94p1 phage was diluted in 100 µl of 0.1 M sodium bicarbonate buffer (pH 8.6), and added to each well of ELISA plate, and coated thereto at 4° C. for 16 hours. After coating, the remaining antigens were removed, and 300 µl of protein-free blocking buffer (Pierce) was added to each well to perform blocking. After blocking, the plate was washed with TBST six times, and treated with the sera of breast cancer patient and normal individual, which were pre-adsorbed with an extract of the phage host cell ER2738, as a primary antibody. The pre-adsorption is a procedure that is generally required for ELISA using the human serum, and was performed in the present invention as follows: Cell lysate of ER2738, which was used as a host cell in phage amplification, was prepared, and an amount corresponding to 50 µg of protein was taken, mixed with $3 \times 10^{10}$ of normal M13 bacteriophage (indicated as Eph) expressing no peptide sequence in 0.5 µl of protein-free blocking solution (Pierce) containing each 2 µl of human serum samples, and reacted at room temperature for 2 hours. After the reaction, 100 µl of the product was used as a primary antibody. The primary antibody reaction was performed at room temperature for 2 hours, and the remaining antibodies after reaction was washed with TBST six times. As a secondary antibody, anti-human IgGAM-HRP (Pierce) was diluted in the protein-free blocking solution at a ratio of 1:5000, and 100 µl thereof was added to the primary antibody treated sample, and reacted at room temperature for 90 minutes. After reaction, the plate was washed with TBST six times, and 100 µl of TMB solution was added for HRP reaction. Absorbance was measured at 450 nm. ELISA for human serum using K94p1 was repeated 4 times or more to ascertain reproducibility, and the representative result is shown in FIG. 11.

As shown in FIG. 11, ELISA using the K94p1 phage distinguished the serum of a breast cancer patient from that of a normal individual with 50% sensitivity and 82.61% specificity. Therefore, human serum ELISA can be performed using the K94p1 phage, which is an epitope mimetic of the autoantibody against CK8/18 complex of the present invention, thereby being utilized as a diagnostic method for breast cancer.

Further, in order to examine whether liver cancer patients can be diagnosed using the K94p1 phage, ELISA was performed for the sera of liver cancer patients in the same manner as above. Since the TAB-K94 antibody was an autoantibody obtained from liver cancer model mouse, its diagnostic effect was expected in the liver cancer as well. However, as shown in FIG. 12, no difference was observed between results from the sera of liver cancer patients and normal individuals, unlike in breast cancer patients.

Taken together, the TAB-K94 autoantibody has a characteristic of recognizing the CK8/18 complex, and its epitope mimetic, K94p1 phage antigen is used to constitute a diagnostic method using ELISA specific to breast cancer.

Example 13

Epitope Sequences Having Reactivity to TAB-K94 Autoantibody

The results of screening cyclic peptide-expressing phage libraries using the TAB-K94 antibody showed that the TAB-K94p1 cyclic peptide having an ISPDAHS sequence (SEQ ID NO. 21) between cysteine sequences at both ends mimics the K94 antibody-specific epitope structure.

Each amino acid of cyclic peptides consisting of 9 amino acids forms the epitope structure to contribute to binding with antibody. In order to examine the contribution of each amino acid of K94p1 peptide to the epitope structure, glycine or alanine substituents for each site were prepared to examine their reactivity to the TAB-K94 antibody. In this regard, MBP (maltose binding protein) was employed as an epitope expression construct, and it was expressed in the form with an insertion of a cyclic peptide sequence (-CX7C-) consisting of 9 amino acids at the C-terminus of MBP.

The reactivity of each peptide variant to TAB-K94 antibody was examined by ELISA (Table 3; reactivity of TAB-K94 antibody to K94p1 peptide antigen was set at 100% as a reference, and relative reactivity of each peptide variant was represented). As a result, most glycine variants showed less than 10% reactivity, when the reactivity of K94p1 sequence peptide antigen was determined as 100%, suggesting that substitution of glycine having no side chain increases structural freedom of the peptide which results in hindrance to form a cyclic peptide structure. It seems that substitution of alanine does not cause difficulty of forming a cyclic structure by the increase in structural freedom, unlike that of glycine. The variants could be divided into groups showing no antibody reactivity (I1A, D4A), showing partial antibody reactivity (relative reactivity of 50% or less: H6A, P3A, D4G), and showing nearly intact antibody reactivity (relative reactivity of 70% or more: S2A, S7A). The groups maintaining the antibody reactivity are alanine substitutions of serine residue, indicating that the side chain hydroxyl group (OH—) of serine virtually does not contribute to antibody reaction. On the contrary, it can be suggested each side chain of the groups showing reduced antibody reactivity greatly contributes to formation of cyclic peptide structure and antibody binding.

TABLE 3

Reactivity of Gly/Ala variants of K94p1 peptide antigen to K94 antibody

| name | Peptide sequence | Rel. binding (%) |
|---|---|---|
| K94p1 | I S P D A H S | 100 |
| I1G | G S P D A H S | 2 |
| S2G | I G P D A H S | 0 |
| P3G | I S G D A H S | 2 |
| D4G | I S P G A H S | 12 |
| A5G | I S P D G H S | 0 |
| H6G | I S P D A G S | 1 |
| S7G | I S P D A H G | 0 |
| I1A | A S P D A H S | 0 |
| S2A | I A P D A H S | 99 |
| P3A | I S A D A H S | 30 |
| D4A | I S P A A H S | 0 |
| H6A | I S P D A A S | 19 |
| S7A | I S P D A H A | 71 |

Taken together, the results suggest that a polypeptide having an amino acid sequence of ISPDAHS represented by SEQ ID NO. 21, ISPGAHS represented by SEQ ID NO. 27, IAPDAHS represented by SEQ ID NO. 28, ISADAHS represented by SEQ ID NO. 29, ISPDAAS represented by SEQ ID NO. 30, or ISPDAHA represented by SEQ ID NO. 31 can be utilized as an antigen mimetic peptide capable of detecting TAB-K94 autoantibody that is used as a breast cancer diagnostic marker having a characteristic of recognizing the CK8/18 complex.

The invention claimed is:

1. An isolated polypeptide comprising:
   (i) an amino acid sequence selected from the group consisting of SEQ ID NO. 21, SEQ ID NO. 22, SEQ ID NO. 27, SEQ ID NO. 28, SEQ ID NO. 29, SEQ ID NO. 30 and SEQ ID NO. 31, and
   (ii) additional cysteines at both ends of said amino acid sequence,
   wherein said isolated polypeptide specifically binds to a cytokeratin 8/18 complex-specific autoantibody.

2. The isolated polypeptide according to claim 1, wherein said additional cysteines consist of a single additional cysteine at each end of said amino acid sequence.

3. A composition for diagnosing breast cancer, comprising a polypeptide agent capable of measuring an expression level of a cytokeratin 8/18 complex-specific autoantibody or a fragment comprising an antigen-binding site thereof, wherein the polypeptide agent comprises:
   (i) an amino acid sequence selected from the group consisting of SEQ ID NO. 21, SEQ ID NO. 22, SEQ ID NO. 27, SEQ ID NO. 28, SEQ ID NO. 29, SEQ ID NO. 30 and SEQ ID NO. 31, and
   (ii) additional cysteines at both ends of said amino acid sequence,
   and wherein said polypeptide agent specifically binds to a cytokeratin 8/18 complex-specific autoantibody.

4. The composition according to claim 3, wherein the autoantibody is an antibody specifically binding to a an amino acid sequence selected from the group consisting of SEQ ID NO. 21, SEQ ID NO. 28 and SEQ ID NO. 31.

5. The composition according to claim 3, wherein said additional cysteines consist of a single additional cysteine at each end of said amino acid sequence.

6. The composition according to claim 3, wherein the polypeptide is a fusion protein of the polypeptide agent and a carrier protein.

7. The composition according to claim 6, wherein the carrier protein is MBP (maltose binding protein).

8. A kit for diagnosing breast cancer comprising the composition of claim 3.

9. The kit according to claim 8, wherein the kit is to use any one of Western blotting, ELISA (Enzyme Linked Immunosorbent Assay), radioimmunoassay, radioimmunodiffusion, Ouchterlony immunodiffusion, rocket immunoelectrophoresis, immunohistostaining, immunoprecipitation as say, complement fixation assay, FACS, or protein chip assay.

* * * * *